US012790300B2

(12) United States Patent
Guida et al.

(10) Patent No.: US 12,790,300 B2
(45) Date of Patent: Nov. 10, 2026

(54) STING MODULATORS, COMPOSITIONS, AND METHODS OF USE

(71) Applicant: University of South Florida, Tampa, FL (US)

(72) Inventors: Wayne Charles Guida, Tampa, FL (US); Kenyon Gregory Daniel, Tampa, FL (US); Wesley Harrell Brooks, Tampa, FL (US); Linette Harding, Tampa, FL (US); Rainer Scott Metcalf, Palm Harbor, FL (US); Sam G. Shrivastava, Tampa, FL (US); James William Leahy, Lutz, FL (US); Robert Sparks, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 1039 days.

(21) Appl. No.: 17/637,773

(22) PCT Filed: Aug. 31, 2020

(86) PCT No.: PCT/US2020/048726
§ 371 (c)(1),
(2) Date: Feb. 23, 2022

(87) PCT Pub. No.: WO2021/042024
PCT Pub. Date: Mar. 4, 2021

(65) Prior Publication Data

US 2022/0267270 A1 Aug. 25, 2022

Related U.S. Application Data

(60) Provisional application No. 62/938,438, filed on Nov. 21, 2019, provisional application No. 62/894,536, filed on Aug. 30, 2019.

(51) Int. Cl.

| | |
|---|---|
| ***A61K 31/455*** | (2006.01) |
| ***A61K 45/06*** | (2006.01) |
| ***A61P 35/00*** | (2006.01) |
| ***A61P 37/00*** | (2006.01) |
| ***C07D 213/80*** | (2006.01) |

(52) U.S. Cl.
CPC ............ *C07D 213/80* (2013.01); *A61K 45/06* (2013.01); *A61P 35/00* (2018.01); *A61P 37/00* (2018.01)

(58) Field of Classification Search
CPC ........ C07D 213/80; A61P 35/00; A61P 37/00; A61K 45/06
See application file for complete search history.

(56) References Cited

U.S. PATENT DOCUMENTS

| | | | |
|---|---|---|---|
| 3,478,040 | A | 11/1969 | Sherlock et al. |
| 4,009,126 | A | 2/1977 | McFarland |
| 4,009,166 | A | 2/1977 | Noda et al. |
| 4,146,621 | A | 3/1979 | Voorhees |
| 4,273,777 | A | 6/1981 | Los |
| 7,514,446 | B2 | 4/2009 | Davis-Ward et al. |
| 7,863,289 | B2 | 1/2011 | Spevak et al. |
| 8,026,247 | B2 | 9/2011 | Bold et al. |
| 8,501,756 | B2 | 8/2013 | Artman, III et al. |
| 8,552,002 | B2 | 10/2013 | Ding et al. |
| 8,815,901 | B2 | 8/2014 | Furet et al. |
| 8,912,204 | B2 | 12/2014 | Ibrahim et al. |
| 8,912,294 | B2 | 12/2014 | Butikofer |
| 9,260,437 | B2 | 2/2016 | Ibrahim et al. |
| 9,273,051 | B2 | 3/2016 | Chen et al. |
| 2009/0118292 | A1 | 5/2009 | Deng et al. |
| 2015/0018336 | A1 | 1/2015 | Chen et al. |
| 2015/0376130 | A1 | 12/2015 | Arvela et al. |
| 2024/0368084 | A1 | 11/2024 | Guida et al. |

FOREIGN PATENT DOCUMENTS

| | | |
|---|---|---|
| CH | 534129 | 2/1973 |
| CH | 550794 | 6/1974 |
| CN | 108947879 | 12/2018 |
| CN | 112624936 A | 4/2021 |
| DE | 1802777 | 6/1969 |
| WO | WO 2000031816 | 6/2000 |
| WO | WO 2007002325 | 1/2007 |
| WO | WO 2007002433 | 1/2007 |
| WO | WO 2007110344 | 10/2007 |
| WO | WO 2008/029199 | 3/2008 |
| WO | WO 2008079903 | 7/2008 |
| WO | WO 2008079906 | 7/2008 |
| WO | WO 2008079909 | 7/2008 |
| WO | WO 2008080001 | 7/2008 |

(Continued)

OTHER PUBLICATIONS

CAS Registry Record for [3-Pyridinecarboxylic acid, 2-[(2,4-dichlorophenyl)amino]-,3-(dimethylamino)propyl ester, hydrochlor], STN Entry Date Nov. 16, 1984. (Year: 1979).*

Kamal, et.al., Synthesis of a new class of 2-anilino substituted nicotinyl arylsulfonylhydrazides as potential anticancer and anti-bacterial agents, Bioorganic & Medicinal Chemistry 15 (2007) pp. 1004-1013. (Year: 2007).*

Lima, et. al., Homologation: A Versatile Molecular Modification Strategy to Drug Discovery, Current Topics in Medicinal Chemistry, 2019, 19, 1734-1750. (Year: 2019).*

(Continued)

*Primary Examiner* — Jeffrey S Lundgren
*Assistant Examiner* — Paul Randall Gauger
(74) *Attorney, Agent, or Firm* — Fish & Richardson P.C.

(57) ABSTRACT

The present disclosure is directed to compounds of Formula (I), or pharmaceutically acceptable salts thereof and compounds of Formula (II), or pharmaceutically acceptable salts thereof, that modulate stimulator of interferon genes (STING), compositions comprising such compounds, and methods of using same for the treatment of disorders such as cancer and autoimmune disease.

21 Claims, 11 Drawing Sheets

(56) References Cited

FOREIGN PATENT DOCUMENTS

| | | |
|---|---|---|
| WO | WO 2008080015 | 7/2008 |
| WO | WO 2009007748 | 1/2009 |
| WO | WO 2009012283 | 1/2009 |
| WO | WO 2009014637 | 1/2009 |
| WO | WO 2009071480 | 6/2009 |
| WO | WO 2009118411 | 10/2009 |
| WO | WO 2009143018 | 11/2009 |
| WO | WO 2009143024 | 11/2009 |
| WO | WO 2009152083 | 12/2009 |
| WO | WO 2010031816 | 3/2010 |
| WO | WO 2010092120 | 8/2010 |
| WO | WO 2010111527 | 9/2010 |
| WO | WO 2010145998 | 12/2010 |
| WO | WO 2011092120 | 8/2011 |
| WO | WO 2012101029 | 8/2012 |
| WO | WO 2012101032 | 8/2012 |
| WO | WO 2012109075 | 8/2012 |
| WO | WO 2012113774 | 8/2012 |
| WO | WO 2012139930 | 10/2012 |
| WO | WO 2012143248 | 10/2012 |
| WO | WO 2012152763 | 11/2012 |
| WO | WO 2013014039 | 1/2013 |
| WO | WO 2013050446 | 4/2013 |
| WO | WO 2013050448 | 4/2013 |
| WO | WO 2013102059 | 7/2013 |
| WO | WO 2014011900 | 1/2014 |
| WO | WO 2014019908 | 2/2014 |
| WO | WO 2014072220 | 5/2014 |
| WO | WO 2014160521 | 10/2014 |
| WO | WO 2014184069 | 11/2014 |
| WO | WO 2014194127 | 12/2014 |
| WO | WO 2015017528 | 2/2015 |
| WO | WO 2015017533 | 2/2015 |
| WO | WO 2015057873 | 4/2015 |
| WO | WO 2015058129 | 4/2015 |
| WO | WO 2015061572 | 4/2015 |
| WO | WO 2015108992 | 7/2015 |
| WO | WO 2015112806 | 7/2015 |
| WO | WO 2015161274 | 10/2015 |
| WO | WO 2015161277 | 10/2015 |
| WO | WO 2015191666 | 12/2015 |
| WO | WO 2015191667 | 12/2015 |
| WO | WO 2016011141 | 1/2016 |
| WO | WO 2016011144 | 1/2016 |
| WO | WO 2016011147 | 1/2016 |
| WO | WO 2016022569 | 2/2016 |
| WO | WO 2016075224 | 5/2016 |
| WO | WO 2016081450 | 5/2016 |
| WO | WO 2021001032 | 1/2021 |
| WO | WO 2021009075 | 1/2021 |
| WO | WO 2021039930 | 3/2021 |
| WO | WO 2021043248 | 3/2021 |
| WO | WO 2021052763 | 3/2021 |

OTHER PUBLICATIONS

Al-Sha'er et al., "Elaborate Ligand-Based Modeling Reveals New Nanomolar Heat Shock Protein 90[alpha] Inhibitors," J. Chem. Inf. Model, Sep. 2010, 50(9):1706-1723.

Gong et al., "Discovery of a novel series of 4-quinolone JNK inhibitors," Bio. Med. Chem. Ltrs., Dec 2012, 22(24):7381-7387.

International Preliminary Report on Patentability in International Application No. PCT/US2022/042493, mailed on Mar. 14, 2024, 7 pages.

International Search Report and Written Opinion in International Application No. PCT/US2022/042493, mailed on Dec. 8, 2022, 22 pages.

PubChem SID No. 347761751, "Clonixeril," retrieved on Nov. 12, 2022, dated Nov. 5, 2029, 7 pages.

Sparks et al., "Discovery of Clonixeril as a Sub-Femtomolar Modulator of the Human STING Receptor," ChemRxiv Preprint, Nov. 19, 2024, Version 2, 43 pages.

Ahn et al., "Self-DNA, STING-dependent signaling and the origins of autoinflammatory disease," Current Opinion in Immunology 2014, 31:121-126.

Berendsen et al., "Molecular-Dynamics with Coupling to an External Bath," Journal of Chemical Physics, 1984, 81(8):3684-3690.

Berman et al., "The protein data bank," Nucleic acids research, 2000, 28(1):235-242.

Bernstein et al., "The Protein data bank. A computer-based archival file for macromolecular structures," European Journal of Biochemistry, 1977, 80(2):319-324.

Blom et al., "Preparative LC-MS Purification: Improved Compound Specific Method Optimization," J. Combi. Chem, 2004, 6(6):874-883.

Bowers et al., "Scalable Algorthms for Molecular Dynamic Simulations on Commodity Clusters," Proceedings of the ACM/IEEE Conference on Supercomputing (SC06), Nov. 2006, 11-17.

Brenner et al., "A review of the application of inflammatory biomarkers in epidemiologic cancer research," Cancer Epidemiol Biomarkers Prev, Sep. 2014, 23(9):1729-1751.

Chin et al., "Novel c-di-GMP recognition modes of the mouse innate immune adaptor protein STING," Acta Crystallographica Section D: Biological Crystallography 69.3 (2013): 352-366.

Cho et al., "Importance of Accurate Charges in Molecular Docking: Quantum Mechanical/Molecular Mechanical (QM/MM) Approach," J. Comput. Chem., Jul. 2005, 26:915-931.

Conlon et al., "Mouse, but not human STING, binds and signals in response to the cascular disrupting agent 5, 6-dimethylxanthenone-4-acetic acid," The Journal of Immunology, May 2013, 190(10):5216-5225.

Darden et al., "Particle mesh ewald-an N. Log(N) method for Ewald sums in large systems," J. Chem. Phys. 1993, 98:10089-10092.

Essmann et al., "A smooth particle mesh Ewald method," J. Chem. Phys. 1995, 103:8577-8593.

Farid et al., "New insights about HERG blockade obtained from protein modeling, potential energy mapping, and docking studies," Bioorg. & Med. Chem., 2006, 14:3160-3173.

Friesner et al., "Extra Precision Glide: Docking and Scoring Incorporating a Model of Hydrophobic Enclosure for Protein-Ligand Complexes," J. Med. Chem., 2006, 49:6177-6196.

Friesner et al., "Glide: A New Approach for Rapid, Accurate Docking and Scoring. 1. Method and Assessment of Docking Accuracy," J. Med. Chem., 2004, 47:1739-1749.

Gao et al., "Structure-function analysis of STING activation by c[G(2',5')pA(3',5')p] and targeting by antiviral DMXAA," Cell, Aug. 2013, 154(4):748-762.

Gao et al., "Activation of cyclic GMP-AMP synthase by self-DNA causes autoimmune diseases," Proceedings of the National Academy of Sciences of the United States of America 2015, 1124(42):E5699-E5705.

gohom.win [online], "Induced Fit Docking Schrodinger Software Release," 20015, retrieved on Apr. 12, 2022, retrieved from URL<http://gohom.win/ManualHom/Schrodinger/Schrodinger_2015-2_docs/inducedfit/inducedfit_user_manual.pdf>, 80 pages.

Guo et al., "Probing the α-Helical Structural Stability of Stapled p53 Peptides: Molecular Dynamics Simulations and Analysis," Chem. Biol. Drug Des., 2010, 75:348-359.

Halgren et al., "Glide: A New Approach for Rapid, Accurate Docking and Scoring. 2. Enrichment Factors in Database Screening," J. Med. Chem., 2004, 47:1750-1759.

Halgren, "Identifying and characterizing binding sites and assessing druggability," J. Chem. Inf. Model., 2009, 49:377-389.

Halgren, "New method for fast and accurate binding-site identification and analysis," Chem. Biol. Drug Des., Feb. 2007, 69:146-148.

Harder et al., "OPLS3: A Force Field Providing Broad Coverage of Drug-like Small Molecules and Proteins," J. Chem. Theory Comput., 2015, 12(1):281-296.

International Preliminary Report on Patentability in International Application No. PCT/US2020/48726, dated Mar. 1, 2022, 7 pages.

International Search Report and Written Opinion in International Application No. PCT/US2020/48726, dated Jan. 19, 2021, 11 pages.

Jin et al., "Identification and characterization of loss-of-function human MPYS variant," Genes Immun., Jun. 2011, 12:263-9.

(56) References Cited

OTHER PUBLICATIONS

Kim et al., "Mammaglobin-A is a target for breast cancer vaccination," OncoImmunology, Feb. 2016, 5(2):e1069940.
Koes et al., "ZINCPharmer: pharmacophore search of the ZINC database," Nucleic acids research, May 2012, 40(W1):W409-W414.
Kubler et al. "Self-adjuvanted mRNA vaccination in advanced prostate cancer patients: a first-in-man phase I/IIa study," Immunother Cancer, Jun. 2015, 3:26.
Li et al., "Interferon signature gene expression is correlated with autoantibody profiles in patients with incomplete lupus syndromes," J. Clin. Exp. Immunol. 2010, 159(3):281-291.
Li et al., "Very fast empirical prediction and rationalization of protein pKa values," Proteins: Structure, Function, and Bioinformatics, 2005, 61(4):704-721.
Liu et al., "Biomarkers of chronic inflammation in disease development and prevention: challenges and opportunities," Nat. Immunol, Oct. 2017, 18(11):1175-1180.
Mulligan, "RET revisited: expanding the oncogenic portfolio," Nature Reviews Cancer, Mar. 2014, 14(3):173-186.
Murphy et al., "A mixed quantum mechanics/molecular mechanics (QM/MM) method for large-scale modeling of chemistry in protein environments," J. Comp. Chem., Dec 2000, 21(16):1442-1457.
Nosé et al., "Constant pressure molecular dynamics for molecular systems," Molecular Physics, 1983, 50(5):1055-1076.
Ott et al., "An immunogenic personal neoantigen vaccine for patients with melanoma," Nature, Jul. 2017, 547:217-221.
Peturssion et al., "Protecting Groups in Carbohydrate Chemistry," J. Chem. Educ, 1997, 74(11):1297-1303.
Philipp et al., "Mixed ab initio QM/MM modeling using frozen orbitals and tests with alanine dipeptide and tetrapeptide," J. Comp. Chem., 1999, 20:1468-1494.
Plosker, "Sipuleucel-T: in metastatic castration-resistant prostate cancer," Drugs Jan. 2011, 71(1):101-108.
Ponder et al., "An efficient newton-like method for molecular mechanics energy minimization of large molecules," Journal of Computational Chemistry, 1987, 8(7):1016-1024.
Price et al., "A modified TIP3P water potential for simulation with Ewald summation," The Journal of chemical physics, 2004, 121(2):10096-10103.
Pubchem-CID: 21312023, "2,3-Dihydroxypropyl 2-(2,6-dimethylanilino)pyridine-3-carboxylate," PubChem, retrieved on Apr. 13, 2022, retrieved from URL<2,3-Dihydroxypropyl 2-(2,6-dimethylanilino)pyridine-3-carboxylate | C17H20N2O4—PubChem (nih.gov)>, 8 pages.
Qiu et al., "The GB/SA continuum model for solvation. A fast analytical method for the calculation of approximate Born radii," The Journal of Physical Chemistry, 1997, A 101.16:3005-3014.
Rausch et al. "mRNA vaccine CV9103 and CV9104 for the treatment of prostate cancer," Human Vaccin Immunother, 2014, 10(11):3146-3152.
Roemer et al., "Molecular and Structural Biomarkers of Inflammation at Two Years After Acute Anterior Cruciate Ligament Injury Do Not Predict Structural Knee Osteoarthritis at Five Years," Arthritis Rheumatol, Feb. 2019, 71(2):238-243.
Ryckaert et al., "Numerical integration of the cartesian equations of motion of a system with constraints: molecular dynamics of n-alkanes," Journal of Computational Physics, 1977, 23(3):327-341.
Sahin et al., "Personalized RNA mutanome vaccines mobilize poly-specific therapeutic immunity against cancer," Nature, Jul. 2017, 547:222-226.
Sastry et al., "Protein and ligand preparation: Parameters, protocols, and influence on virtual screening enrichments," J. Comput. Aid. Mol. Des., Mar. 2013, 27(3):221-234.
Schrodinger.com [online], "Desmond High-performance molecular dynamics simulations," 2017, retrieved on Apr. 13, 2022, retrieved from URL<schrodinger.com/products/desmond>, 4 pages.
Schrodinger.com [online], "LigPrep," 2017, retrieved on Apr. 12, 2022, retrieved from URL<https://www.schrodinger.com/products/ligprep>, 3 pages.
Schrodinger.com [online], "Maestro," available on or before Mar. 2021, retrieved on Apr. 12, 2022, retrieved from URL<https://www.schrodinger.com/products/maestro>, 12 pages.
Schrodinger.com [online], "Prime," 2017, retrieved on Apr. 13, 2022, retrieved from URL<https://www.schrodinger.com/products/prime>, 3 pages.
Schrodinger.com [online], "Protein Preparation Wizard," available on or before 2021, retrieved on Apr. 12, 2022, retrieved from URL<https://www.schrodinger.com/science-articles/protein-preparation-wizard>, 6 pages.
Schrödinger.com [online], "QM-Polarized Ligand Docking protocol, " 2017, retrieved on Apr. 12, 2022; retrieved from URL<https://www.schrodinger.com/science-articles/qm-polarized-ligand-docking>, 4 pages.
Schrodinger.com [online], "SiteMap," 2017, retrieved on Apr. 12, 2022, retrieved from URL<https://www.schrodinger.com/products/sitemap>, 3 pages.
Shang et al., "Crystal structures of STING protein reveal basis for recognition of cyclic di-GMP," Nature structural and molecular biology, 2012, 19(7):725.
Sherman et al., "Novel Procedure for Modeling Ligand/Receptor Induced Fit Effects," J. Med. Chem., 2006, 49:534-553.
Sherman et al., "Use of an Induced Fit Receptor Structure in Virtual Screening," Chemical Biology & Drug Design, 2006, 67:83-84.
Shivakumar et al., "Prediction of Absolute Solvation Free Energies using Molecular Dynamics Free Energy Perturbation and the OPLS Force Field," J. Chem. Theory Comput, 2010, 6(5):1509-1519.
Shu et al., "Structure of STING bound to cyclic di-GMP reveals the mechanism of cyclic dinucleotide recognition by the immune system," Nature structural and molecular biology, Jun. 2012, 19(7):722-724.
Tanaka et al., "STING specifies IRF3 phosphorylation by TBK1 in the cytosolic DNA signaling pathway," Science signaling, 2012, 5(214):ra20-ra20.
Tuckerman et al., "Reversible multiple time scale molecular dynamics," The Journal of chemical physics, 1992, 97(3):1990-2001.
Yi et al., "Single nucleotide polymorphisms of human STING can affect innate immune response to cyclic dinucleotides," PLoS One, Oct. 2013, 8(10):e77846.
Zakynthinos et al., "Inflammatory biomarkers in coronary artery disease," Journal of Cardiology, Jun. 2009, 53(3):317-333.
Zhang et al., "Cyclic GMP-AMP containing mixed phosphodiester linkages is an endogenous high-affinity ligand for STING," 2013, Mol. Cell. 51:226-235.
Zhou et al., "The triggers of the cGAS-STING pathway and the connection with inflammatory and autoimmune diseases," Infection, Genetics, and Evolution, Jan. 2020, 77:104094.
Extended European Search Report in European Appln. No. 22865617.9, dated Jul. 10, 2025, 9 pages.
Extended European Search Report in European Appln. No. 20859460.6, dated Oct. 17, 2023, 12 pages.

* cited by examiner

MS Spectrum

MS Zoomed Spectrum

MS Spectrum Peak List

| m/z | z | Abund | Formula | Ion |
|---|---|---|---|---|
| 337.0965 | 1 | 644544.25 | C16H18CN2O4 | (M+H)+ |
| 338.0993 | 1 | 103974.52 | C16H18CN2O4 | (M+H)+ |
| 339.0944 | 1 | 197430.81 | C16H18CN2O4 | (M+H)+ |
| 340.0963 | 1 | 30993.1 | C16H18CN2O4 | (M+H)+ |
| 341.0985 | 1 | 3793.27 | C16H18CN2O4 | (M+H)+ |

| Structure | Compound | H185 Distance (Angstroms) | Model $k_D$ (nM) | ITC $k_D$ (nM) | Cell $EC_{50}$ (nM) |
|---|---|---|---|---|---|
| $hSTING^{WT}$ | c-2'3'-GAMP | 35.0 | 2.4 | 3.8 | 42 (IFNb mRNA) |
| | c-2'2'-GAMP | - | 256 | 287 | 16 (IFNb mRNA) |
| | c-di-GMP | - | 6377 | 1210 | 538 (IFNb mRNA) |
| $hSTING^{REF}$ | c-2'3'-GAMP | 34.7 | 784 | 5300[b] | 1200 ELISA |
| | c-2'2'-GAMP | 38.4 | 236 | 2500 | 3400 ELISA |
| | c-di-GMP | 41.4 | 1300 | 4600[c] | ND (IFNb Luc) |
| | | | | 4420[d] | ND (IFNb Luc) |

STING MODULATORS, COMPOSITIONS, AND METHODS OF USE

CROSS-REFERENCE TO RELATED APPLICATIONS

This application is a U.S. National Phase Application of International Application No. PCT/US2020/048726, filed on Aug. 31, 2020, which claims priority to U.S. Provisional Application No. 62/894,536, filed on Aug. 30, 2019; and U.S. Provisional Application No. 62/938,438, filed on Nov. 21, 2019; each of which is incorporated by reference herein in its entirety.

BACKGROUND

Cancer is one of the world's most dreaded diseases. Tumor cells are hard to eliminate due their aberrant genetics, which results in uncontrolled growth. For example, "cold tumors" are a type of tumor that is not recognized and eradicated by the immune system. The STING (STimulator of INterferon Genes) pathway is involved in the innate immune response, which can help combat cancer, as well as cause certain autoimmune disorders such as systemic lupus erythematosus (SLE) and other diseases that are associated with an accumulation of nucleic acids in the cytoplasm.

STING-mediated production of IFN-β within the tumor microenvironment can result in activation of tumor antigen-specific $CD8^+$ T-cell immunity that can lead to tumor regression. Mechanistic studies have shown that STING induced anti-tumor immunity is likely due to a pro-inflammatory cytokine response as well as the tumor specific $CD8^+$ T-cellular response. STING activation by STING agonists should result in innate T-cell mediated anti-tumor immunity in the tumor microenvironment and have significant potential as a therapeutic strategy for the treatment of patients with advanced solid tumors. On the other hand, inhibition of STING (by STING antagonists) would lead to a decreased production of IFN-β and other Interferon Stimulated Genes (ISG) which are comprised of approximately 300 cytokines induced by the transcription factors interferon regulatory factor 3 (IRF3) and nuclear factor kappa-light-chain-enhancer of activated B cells (NF-κB). Inhibiting STING could have implications in the treatment of autoimmune disease such as lupus erythematosus.

Recently, there has been interest in developing agonists to increase activity of the STING pathway as a modality for cancer treatment. Most STING agonists developed to date have been cyclic di-nucleotides (CDNs). In contrast, rather than activating STING to provoke an immune anti-tumor response, STING antagonists reduce anti-DNA antibody production resulting from abnormal removal of cytoplasmic DNA in immune cells. This leads to the accumulation of autoantibodies, chronic inflammation, and organ dysfunction that are hallmarks of SLE. In addition to SLE, accumulation of abnormal levels of cytoplasmic or lysosomal DNA (leading to STING activation) relate to several other diseases, including viral infections.

SUMMARY

Some embodiments provide a compound of Formula (I), or a pharmaceutically acceptable salt thereof:

(I)

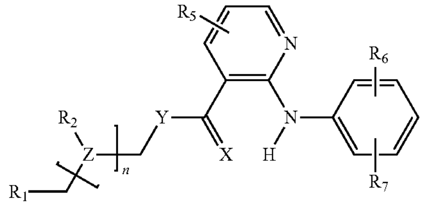

wherein X, Y, Z, $R^1$, $R^2$, $R^{3A}$, $R^4$, $R^{4A}$, $R^5$, $R^6$, $R^7$, $R^8$, $R^9$, and $R^{10}$, are as defined herein.

Some embodiments, provide compounds of Formula (II), or pharmaceutically acceptable salts thereof.

(II)

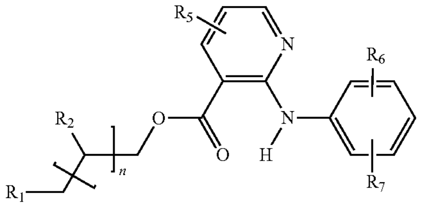

wherein n, $R^1$, $R^2$, $R^3$, $R^{3A}$, $R^4$, $R^5$, $R^6$, $R^7$, $R^8$, $R^9$, and $R^{10}$, are as defined herein.

Some embodiments provide a method of treating cancer comprising administering a therapeutically effective amount of a compound of Formula (I), or a pharmaceutically acceptable salt thereof, to a subject in need thereof. Some embodiments provide a method of treating cancer comprising administering a therapeutically effective amount of a compound of Formula (II), or a pharmaceutically acceptable salt thereof, to a subject in need thereof.

Some embodiments provide a method of treating an autoimmune disorder comprising administering a therapeutically effective amount of a compound of Formula (I), or a pharmaceutically acceptable salt thereof, to a subject in need thereof. Some embodiments provide a method of treating an autoimmune disorder comprising administering a therapeutically effective amount of a compound of Formula (II), or a pharmaceutically acceptable salt thereof, to a subject in need thereof.

DETAILED DESCRIPTION

Figure 1:
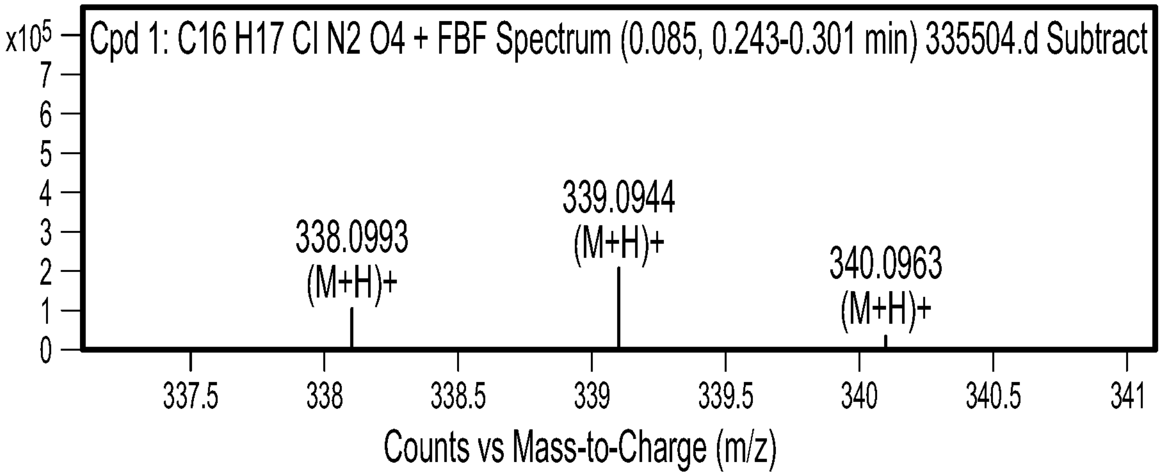
FIG. 1 illustrates a mass spectrum, a zoomed mass spectrum, and a peak table of NSC335504.
Figure 1:
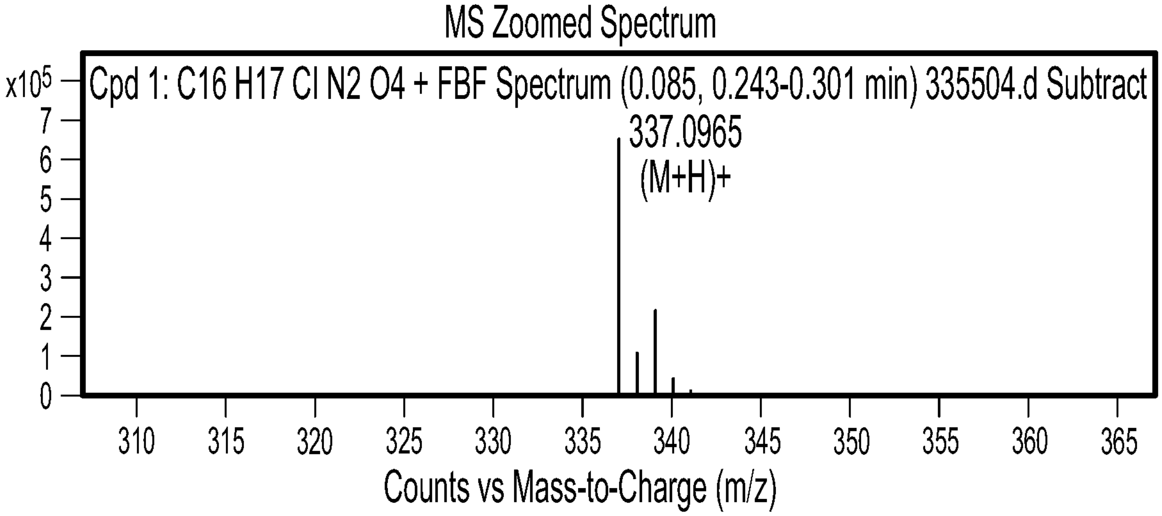

Some embodiments, provide compounds of Formula (I),

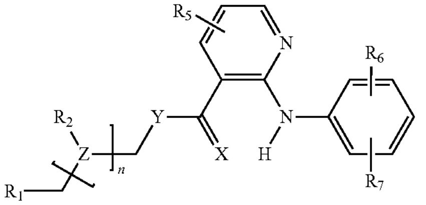

(I)

or pharmaceutically acceptable salts thereof, wherein:

X is O or $NR^{4A}$;

Y is O, $NR^{4A}$, $CH_2$, or absent;

Z is N or CH;

n is 0, 1, 2, or 3;

$R^1$ and $R^2$ are independently selected from OH, $OR^3$, $OR^{3A}$, $SR^3$, and $NR^3R^4$;

$R^3$, $R^4$, and $R^{4A}$ are independently selected from hydrogen, C1-C10 alkyl optionally substituted with 1-6 halogens, C6-C10 aryl, and 5 to 10 membered heteroaryl; or $R^3$ and $R^4$, together with the nitrogen atom to which they are attached, can come together to form a 3 to 7 membered heterocyclyl or 5 to 10 membered heteroaryl;

$R^{3A}$ is

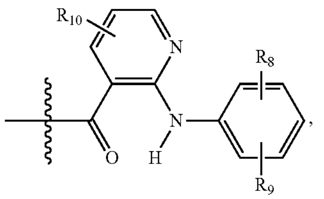

wherein ∿ represents the point of connection of $R^{3A}$ to the remainder of the molecule;

$R^5$, $R^6$, $R^7$, $R^8$, $R^9$, and $R^{10}$ are independently selected from hydrogen, halogen, pseudohalogen, C1-C10 alkyl optionally substituted with 1-6 halogens, C6-C10 aryl, and 5 to 10 membered heteroaryl;

wherein $R^1$ and $R^2$ are not both $OR^{3A}$; and wherein the compound of Formula (I), or a pharmaceutically acceptable salt thereof, is not NCS 335504, or a salt thereof:

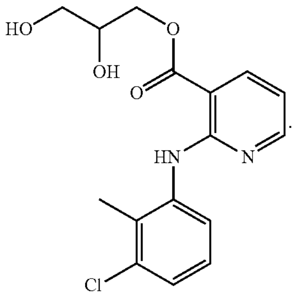 [SMILES: Cc1c(Cl)cccc1Nc1ncccc1C(=O)OCC(O)CO]

.

In some embodiments, X is O. In other embodiments, X is $NR^{4A}$. In some embodiments, Y is O. In other embodiments, Y is $NR^{4A}$. In still other embodiments, Y is $CH_2$. In some embodiments, Y is absent. In some embodiments, Z is N. In other embodiments, Z is CH.

In some embodiments, $R^1$ and $R^2$ are independently selected from OH, $OR^3$, $OR^{3A}$, $SR^3$, and $NR^3R^4$. In some embodiments, $R^1$ is $OR^{3A}$ and $R^2$ is selected from OH, $OR^3$, $SR^3$, and $NR^3R^4$.

In some embodiments, $R^{4A}$ is hydrogen.

In some embodiments, $R^{4A}$ is C1-C10 alkyl optionally substituted with 1-6 halogens. In some embodiments, $R^{4A}$ is C1-C10 alkyl optionally substituted with 1-3 halogens. In some embodiments, $R^{4A}$ is C1-C10 alkyl optionally substituted with 1-3 fluoro. In some embodiments, $R^{4A}$ is C1-C6 alkyl optionally substituted with 1-3 halogens. In some embodiments, $R^{4A}$ is C1-C3 alkyl optionally substituted with 1-3 halogens. In some embodiments, $R^{4A}$ is C1-C6 alkyl optionally substituted with 1-3 fluoro.

In some embodiments, $R^{4A}$ is an unsubstituted C1-C6 alkyl. In some embodiments, $R^{4A}$ is an unsubstituted C1-C3 alkyl. In some embodiments, $R^{4A}$ is methyl.

In some embodiments, $R^{4A}$ is C1-C10 alkyl substituted with 1-6 halogens. In some embodiments, $R^{4A}$ is C1-C10 alkyl substituted with 1-3 halogens. In some embodiments, $R^{4A}$ is C1-C10 alkyl substituted with 1-3 fluoro. In some embodiments, $R^{4A}$ is C1-C6 alkyl substituted with 1-3 halogens. In some embodiments, $R^{4A}$ is C1-C3 alkyl substituted with 1-3 halogens. In some embodiments, $R^{4A}$ is C1-C6 alkyl substituted with 1-3 fluoro. In some embodiments, $R^{4A}$ is trifluoromethyl.

In some embodiments, $R^{4A}$ is C6-C10 aryl, such as phenyl or napthyl. In some embodiments, $R^{4A}$ is 5 to 10 membered heteroaryl, such as pyrrole, imidazole, pyridine, pyrimidine, or quinoline.

In some embodiments, n is 0. In some embodiments, n is 1. In some embodiments, n is 2. In some embodiments, n is 3.

In some embodiments, $R^1$ and $R^2$ are independently selected from OH, $OR^3$, and $OR^{3A}$. In some embodiments, $R^1$ is $OR^{3A}$ and $R^2$ is selected from OH and $OR^3$. In some embodiments, $R^3$ is hydrogen. In some embodiments, $R^3$ is C1-C10 alkyl optionally substituted with 1-6 halogens. In some embodiments, $R^3$ is an unsubstituted C1-C10 alkyl. In some embodiments, $R^3$ is an unsubstituted C1-C6 alkyl. In some embodiments, $R^3$ is methyl.

In some embodiments, $R^3$ is C1-C6 alkyl optionally substituted with 1-3 halogens. In some embodiments, each halogen is fluoro. In some embodiments, $R^3$ is trifluoromethyl. In some embodiments, $R^3$ is C6-C10 aryl, such as phenyl or napthyl. In some embodiments, $R^3$ is 5 to 10 membered heteroaryl, such as pyrrole, imidazole, pyridine, pyrimidine, or quinoline.

In some embodiments, $R^4$ is hydrogen. In some embodiments, $R^4$ is C1-C10 alkyl optionally substituted with 1-6 halogens. In some embodiments, $R^4$ is methyl. In some embodiments, $R^4$ is trifluoromethyl. In some embodiments, $R^4$ is C6-C10 aryl, such as phenyl or napthyl. In some embodiments, $R^4$ is 5 to 10 membered heteroaryl, such as pyrrole, imidazole, pyridine, pyrimidine, or quinoline.

In some embodiments, $R^3$ and $R^4$, together with the nitrogen atom to which they are attached, come together to form a 3 to 7 membered heterocyclyl. In some embodiments, $R^3$ and $R^4$, together with the nitrogen atom to which they are attached, come together to form a 5 to 10 membered heteroaryl.

In some embodiments, $R^{3A}$ is

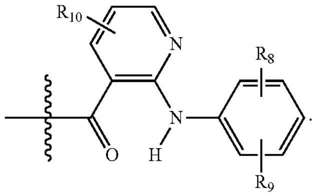

In some embodiments, $R^{3A}$ is

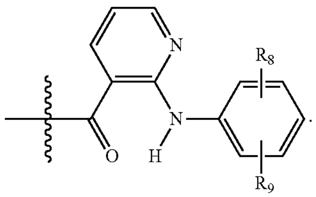

In some embodiments, when Z is CH, $R^1$ and $R^2$ are not both OH. In some embodiments, when X and Y are both O, $R^1$ and $R^2$ are not both OH. In some embodiments, when $R^5$ is hydrogen and Z is CH, $R^1$ and $R^2$ are not both OH. In some embodiments, when Z is CH, X and Y are both O, and $R^5$ is hydrogen, $R^1$ and $R^2$ are not both OH. In some embodiments, compounds of Formula (I), or pharmaceutically acceptable salts thereof, function as STING agonists. In other embodiments, compounds of Formula (I), or pharmaceutically acceptable salts thereof, function as partial STING agonists. In still other embodiments, compounds of Formula (I), or pharmaceutically acceptable salts thereof, function as partial or full STING antagonists.

Some embodiments provide compounds of Formula (II), or pharmaceutically acceptable salts thereof, (II)

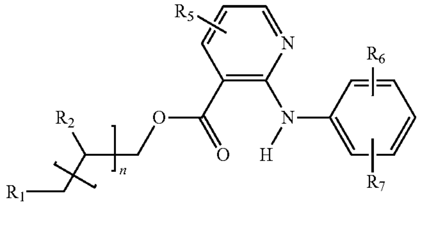

wherein n is 0, 1, 2, or 3;

$R^1$ is

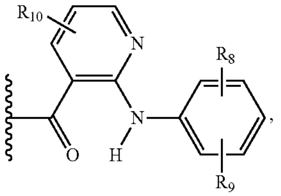

wherein 〰 represents the point of connection of $R^1$ to the remainder of the molecule;

$R^2$ is hydrogen, OH, $OR^3$, $SR^3$, or $NR^3R^4$;

$R^3$ and $R^4$ are independently selected from hydrogen, C1-C10 alkyl optionally substituted with 1-6 halogens, C6-C10 aryl, and 5 to 10 membered heteroaryl; or $R^3$ and $R^4$, together with the nitrogen atom to which they are attached, can come together to form a 3 to 7 membered heterocyclyl or 5 to 10 membered heteroaryl; and $R^5$, $R^6$, $R^7$, $R^8$, $R^9$, and $R^{10}$ are independently selected from hydrogen, halogen, pseudohalogen, C1-C10 alkyl optionally substituted with 1-6 halogens, C6-C10 aryl, and 5 to 10 membered heteroaryl.

Some embodiments provide compounds of Formula (II), or pharmaceutically acceptable salts thereof:

(II)

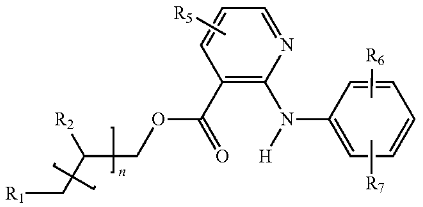

wherein n is 0, 1, 2, or 3;

$R^1$ is

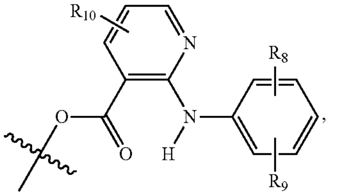

wherein 〰 represents the point of connection of $R^1$ to the remainder of the molecule;

$R^2$ is hydrogen, OH, $OR^3$, $SR^3$, or $NR^3R^4$;

$R^3$ and $R^4$ are independently selected from hydrogen, C1-C10 alkyl optionally substituted with 1-6 halogens, C6-C10 aryl, and 5 to 10 membered heteroaryl; or $R^3$ and $R^4$, together with the nitrogen atom to which they are attached, can come together to form a 3 to 7 membered heterocyclyl or 5 to 10 membered heteroaryl; and $R^5$, $R^6$, $R^7$, $R^8$, $R^9$, and $R^{10}$ are independently selected from hydrogen, halogen, pseudohalogen, C1-C10 alkyl optionally substituted with 1-6 halogens, C6-C10 aryl, and 5 to 10 membered heteroaryl.

Some embodiments provide compounds of Formula (II), or pharmaceutically acceptable salts thereof:

(II)

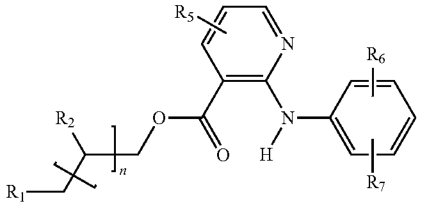

wherein n is 0, 1, 2, or 3;

$R^1$ is

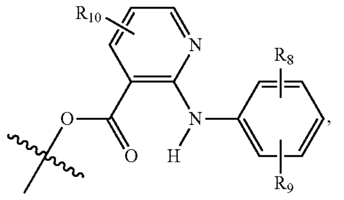

wherein ~ represents the point of connection of $R^1$ to the remainder of the molecule;

$R^2$ is hydrogen, OH, $OR^3$, $SR^3$, or $NR^3R^4$;

$R^3$ and $R^4$ are independently selected from hydrogen, C1-C10 alkyl optionally substituted with 1-6 halogens, C6-C10 aryl, and 5 to 10 membered heteroaryl; or $R^3$ and $R^4$, together with the nitrogen atom to which they are attached, can come together to form a 3 to 7 membered heterocyclyl or 5 to 10 membered heteroaryl; and $R^5$, $R^6$, $R^7$, $R^8$, $R^9$, and $R^{10}$ are independently selected from hydrogen, halogen, pseudohalogen, C1-C10 alkyl optionally substituted with 1-6 halogens, C6-C10 aryl, and 5 to 10 membered heteroaryl; with the proviso that the compound of Formula (II) is not the compound shown below:

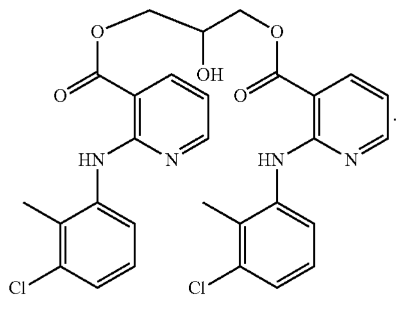 [SMILES: Cc1c(Cl)cccc1Nc1ncccc1C(=O)OCC(O)COC(=O)c1cccnc1Nc1cccc(Cl)c1C]

Some embodiments provide compounds of Formula (II), or pharmaceutically acceptable salts thereof:

(II)

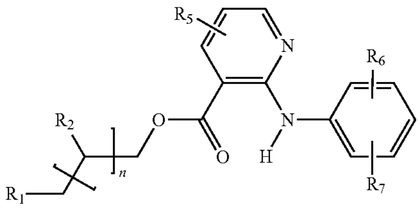

wherein n is 0, 1, 2, or 3;

$R^1$ is

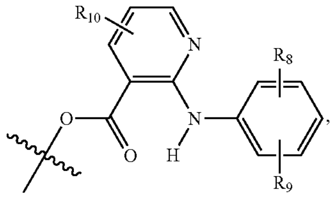

wherein ~ represents the point of connection of $R^1$ to the remainder of the molecule;

$R^2$ is hydrogen, OH, $OR^3$, $SR^3$, or $NR^3R^4$;

$R^3$ and $R^4$ are independently selected from hydrogen, C1-C10 alkyl optionally substituted with 1-6 halogens, C6-C10 aryl, and 5 to 10 membered heteroaryl; or $R^3$ and $R^4$, together with the nitrogen atom to which they are attached, can come together to form a 3 to 7 membered heterocyclyl or 5 to 10 membered heteroaryl;

$R^5$, $R^6$, $R^7$, and $R^{10}$ are independently selected from hydrogen, halogen, pseudohalogen, C1-C10 alkyl optionally substituted with 1-6 halogens, C6-C10 aryl, and 5 to 10 membered heteroaryl; and $R^8$ and $R^9$ are independently selected from hydrogen, fluoro, bromo, iodo, pseudohalogen, C1-C10 alkyl optionally substituted with 1-6 halogens, C6-C10 aryl, and 5 to 10 membered heteroaryl.

In some embodiments, n is 0. In some embodiments, n is 1. In some embodiments, n is 2. In some embodiments, n is 3.

In some embodiments, $R^2$ is hydrogen. In some embodiments, $R^2$ is OH. In some embodiments, $R^2$ is $OR^3$. In some embodiments, $R^2$ is $SR^3$. In some embodiments, $R^2$ is $NR^3R^4$.

In some embodiments, $R^3$ is hydrogen. In some embodiments, $R^3$ is C1-C10 alkyl optionally substituted with 1-6 halogens. In some embodiments, $R^3$ is methyl. In some embodiments, $R^3$ is trifluoromethyl. In some embodiments, $R^3$ is C6-C10 aryl, such as phenyl or napthyl. In some embodiments, $R^3$ is 5 to 10 membered heteroaryl.

In some embodiments, $R^4$ is hydrogen. In some embodiments, $R^4$ is C1-C10 alkyl optionally substituted with 1-6 halogens. In some embodiments, $R^4$ is methyl. In some embodiments, $R^4$ is trifluoromethyl. In some embodiments, $R^4$ is C6-C10 aryl. In some embodiments, $R^4$ is 5 to 10 membered heteroaryl.

In some embodiments, $R^3$ and $R^4$, together with the nitrogen atom to which they are attached, come together to form a 3 to 7 membered heterocyclyl. In some embodiments, $R^3$ and $R^4$, together with the nitrogen atom to which they are attached, come together to form a 5 to 10 membered heteroaryl.

In some embodiments, $R^1$ is

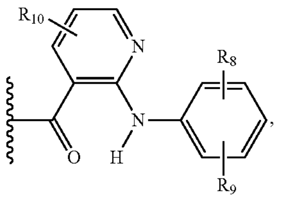

wherein ~~~ represents the point of connection of $R^1$ to the remainder of the molecule.

In some embodiments, $R^5$ is halogen. In some embodiments, $R^5$ is fluoro or chloro. In some embodiments, $R^5$ is pseudohalogen.

In some embodiments, $R^5$ is C1-C10 alkyl optionally substituted with 1-6 halogens. In some embodiments, $R^5$ is C1-C6 alkyl optionally substituted with 1-6 halogens. In some embodiments, $R^5$ is C1-C6 alkyl optionally substituted with 1-3 halogens. In some embodiments, $R^5$ is C1-C3 alkyl optionally substituted with 1-3 halogens. In some embodiments, $R^5$ is C1-C6 alkyl substituted with 1-6 halogens. In some embodiments, $R^5$ is C1-C6 alkyl substituted with 1-3 halogens. In some embodiments, $R^5$ is C1-C3 alkyl substituted with 1-3 halogens. In some embodiments, $R^5$ is an unsubstituted C1-C10 alkyl. In some embodiments, $R^5$ is an unsubstituted C1-C6 alkyl. In some embodiments, $R^5$ is an unsubstituted C1-C3 alkyl. In some embodiments, $R^5$ is methyl. In some embodiments, $R^5$ is trifluoromethyl.

In some embodiments, $R^5$ is C6-C10 aryl. In some embodiments, $R^5$ is 5 to 10 membered heteroaryl.

In some embodiments, $R^6$ is halogen. In some embodiments, $R^6$ is fluoro or chloro. In some embodiments, $R^6$ is pseudohalogen.

In some embodiments, $R^6$ is C1-C10 alkyl optionally substituted with 1-6 halogens. In some embodiments, $R^6$ is C1-C6 alkyl optionally substituted with 1-6 halogens. In some embodiments, $R^6$ is C1-C6 alkyl optionally substituted with 1-3 halogens. In some embodiments, $R^6$ is C1-C3 alkyl optionally substituted with 1-3 halogens. In some embodiments, $R^6$ is C1-C6 alkyl substituted with 1-6 halogens. In some embodiments, $R^6$ is C1-C6 alkyl substituted with 1-3 halogens. In some embodiments, $R^6$ is C1-C3 alkyl substituted with 1-3 halogens. In some embodiments, $R^6$ is an unsubstituted C1-C10 alkyl. In some embodiments, $R^6$ is an unsubstituted C1-C6 alkyl. In some embodiments, $R^6$ is an unsubstituted C1-C3 alkyl. In some embodiments, $R^6$ is methyl. In some embodiments, $R^6$ is trifluoromethyl.

In some embodiments, $R^6$ is C6-C10 aryl. In some embodiments, $R^6$ is 5 to 10 membered heteroaryl.

In some embodiments, $R^7$ is halogen. In some embodiments, $R^7$ is fluoro or chloro. In some embodiments, $R^7$ is pseudohalogen.

In some embodiments, $R^7$ is C1-C10 alkyl optionally substituted with 1-6 halogens. In some embodiments, $R^7$ is C1-C6 alkyl optionally substituted with 1-6 halogens. In some embodiments, $R^7$ is C1-C6 alkyl optionally substituted with 1-3 halogens. In some embodiments, $R^7$ is C1-C3 alkyl optionally substituted with 1-3 halogens. In some embodiments, $R^7$ is C1-C6 alkyl substituted with 1-6 halogens. In some embodiments, $R^7$ is C1-C6 alkyl substituted with 1-3 halogens. In some embodiments, $R^7$ is C1-C3 alkyl substituted with 1-3 halogens. In some embodiments, $R^7$ is an unsubstituted C1-C10 alkyl. In some embodiments, $R^7$ is an unsubstituted C1-C6 alkyl. In some embodiments, $R^7$ is an unsubstituted C1-C3 alkyl. In some embodiments, $R^7$ is methyl. In some embodiments, $R^7$ is trifluoromethyl.

In some embodiments, $R^7$ is C6-C10 aryl. In some embodiments, $R^7$ is 5 to 10 membered heteroaryl.

In some embodiments, $R^8$ is halogen. In some embodiments, $R^8$ is fluoro or chloro. In some embodiments, $R^8$ is pseudohalogen.

In some embodiments, $R^8$ is C1-C10 alkyl optionally substituted with 1-6 halogens. In some embodiments, $R^8$ is C1-C6 alkyl optionally substituted with 1-6 halogens. In some embodiments, $R^8$ is C1-C6 alkyl optionally substituted with 1-3 halogens. In some embodiments, $R^8$ is C1-C3 alkyl optionally substituted with 1-3 halogens. In some embodiments, $R^8$ is C1-C6 alkyl substituted with 1-6 halogens. In some embodiments, $R^8$ is C1-C6 alkyl substituted with 1-3 halogens. In some embodiments, $R^8$ is C1-C3 alkyl substituted with 1-3 halogens. In some embodiments, $R^8$ is an unsubstituted C1-C10 alkyl. In some embodiments, $R^8$ is an unsubstituted C1-C6 alkyl. In some embodiments, $R^8$ is an unsubstituted C1-C3 alkyl. In some embodiments, $R^8$ is methyl. In some embodiments, $R^8$ is trifluoromethyl.

In some embodiments, $R^8$ is C6-C10 aryl. In some embodiments, $R^8$ is 5 to 10 membered heteroaryl.

In some embodiments, $R^9$ is halogen. In some embodiments, $R^9$ is fluoro or chloro.

In some embodiments, $R^9$ is pseudohalogen. In some embodiments, $R^9$ is C1-C10 alkyl optionally substituted with 1-6 halogens. In some embodiments, $R^9$ is methyl. In some embodiments, $R^9$ is trifluoromethyl. In some embodiments, $R^9$ is C6-C10 aryl. In some embodiments, $R^9$ is 5 to 10 membered heteroaryl.

In some embodiments, $R^{10}$ is halogen. In some embodiments, $R^{10}$ is fluoro or chloro. In some embodiments, $R^{10}$ is pseudohalogen.

In some embodiments, $R^{10}$ is C1-C10 alkyl optionally substituted with 1-6 halogens. In some embodiments, $R^{10}$ is C1-C6 alkyl optionally substituted with 1-6 halogens. In some embodiments, $R^{10}$ is C1-C6 alkyl optionally substituted with 1-3 halogens. In some embodiments, $R^{10}$ is C1-C3 alkyl optionally substituted with 1-3 halogens. In some embodiments, $R^{10}$ is C1-C6 alkyl substituted with 1-6 halogens. In some embodiments, $R^{10}$ is C1-C6 alkyl substituted with 1-3 halogens. In some embodiments, $R^{10}$ is C1-C3 alkyl substituted with 1-3 halogens. In some embodiments, $R^{10}$ is an unsubstituted C1-C10 alkyl. In some embodiments, $R^{10}$ is an unsubstituted C1-C6 alkyl. In some embodiments, $R^{10}$ is an unsubstituted C1-C3 alkyl. In some embodiments, $R^{10}$ is methyl. In some embodiments, $R^{10}$ is trifluoromethyl.

In some embodiments, $R^{10}$ is C6-C10 aryl. In some embodiments, $R^{10}$ is 5 to 10 membered heteroaryl.

In some embodiments, when there are greater than one $R^2$, the greater than one $R^2$ are the same. In some embodiments, $R^5$ and $R^{10}$ are the same. In some embodiments, $R^5$ and $R^{10}$ are different. In some embodiments, $R^5$ and $R^{10}$ are independently selected from hydrogen, methyl, and fluoro. In some embodiments, $R^5$ and $R^{10}$ are the same, and are selected from hydrogen, methyl, and fluoro. In some embodiments, $R^5$ and $R^{10}$ are both hydrogen. In some embodiments, $R^6$ and one of $R^8$ and $R^9$ are the same, and $R^7$ and the other of $R^8$ and $R^9$ are the same.

In some embodiments, n is 2, and each $R^2$ is hydrogen. In some embodiments, n is 2, and each $R^2$ is hydroxyl. In some embodiments, $R^6$, $R^7$, $R^8$, and $R^9$ are independently selected from methyl, trifluoromethyl, fluoro, and chloro. In some embodiments, n is 2, each $R^2$ is hydrogen, and $R^5$ and $R^{10}$ are both hydrogen.

In some embodiments, the compound is compound 1:

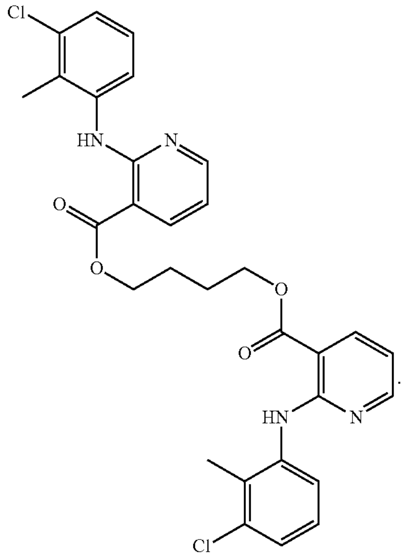

1

In some embodiments, the compound is compound 2:

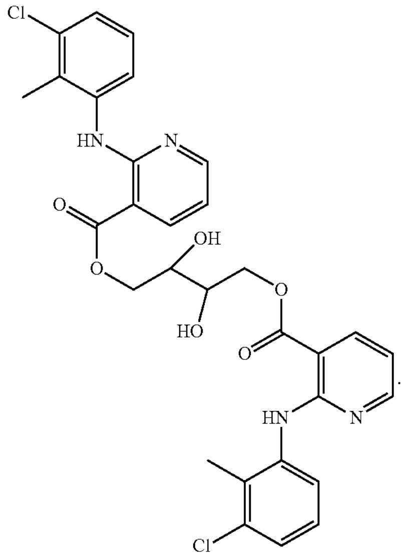

2

In some embodiments, compounds of Formula (II), or pharmaceutically acceptable salts thereof, function as STING agonists. In other embodiments, compounds of Formula (II), or pharmaceutically acceptable salts thereof, function as partial STING agonists. In still other embodiments, compounds of Formula (II), or pharmaceutically acceptable salts thereof, partial or full STING antagonists.

Methods of Use

Some embodiments provide a method of agonizing or partially agonizing the STING pathway in a subject in need thereof, comprising administering a compound of Formula (I) and/or Formula (II), or a pharmaceutically acceptable salt thereof to the subject. In some embodiments, agonizing or partially agonizing the STING pathway in a subject comprises increasing production of IFN-β in the subject. In some embodiments, agonizing or partially agonizing the STING pathway in a subject comprises activating or increasing T-cell immunity. In some embodiments, agonizing or partially agonizing the STING pathway in a subject comprises activating or increasing $CD8^+$ T-cell immunity. In some embodiments, agonizing or partially agonizing the STING pathway in a subject comprises activating or increasing tumor antigen-specific $CD8^+$ T-cell immunity. In some embodiments, increasing T-cell immunity comprises increasing the T-cell population. In some embodiments, the T-cell population is increased by about 20% to about 200%, for example, about 20% to about 80%, about 60% to about 120%, about 100% to about 160%, about 140% to about 200%, or any value in between.

Some embodiments provide a method of antagonizing the STING pathway in a subject in need thereof, comprising administering a compound of Formula (I) and/or Formula (II), or a pharmaceutically acceptable salt thereof, to the subject. In some embodiments, antagonizing the STING pathway in a subject comprises reducing expression of IFN-β in the subject. In some embodiments, antagonizing the STING pathway in a subject comprises reducing expression of one or more cytokines in the subject. In some embodiments, production of IFN-β is decreased by about 10% to about 99%, for example, about 10% to about 30%, about 20% to about 40%, about 30% to about 50%, about 40% to about 60%, about 50% to about 70%, about 60% to about 80%, about 70% to about 90%, about 80% to about 99%, or any value in between. In some embodiments, antagonizing the STING pathway in a subject comprises reducing expression of one or more cytokines in the subject. In some embodiments, the expression of one or more cytokines is decreased by about 10% to about 99%, for example, about 10% to about 30%, about 20% to about 40%, about 30% to about 50%, about 40% to about 60%, about 50% to about 70%, about 60% to about 80%, about 70% to about 90%, about 80% to about 99%, or any value in between. In some embodiments, the one or more cytokines (e.g., two or more, five or more, ten or more, up to twenty or fifty) cytokines. In some embodiments, the one or more cytokines are induced by IRF3. In some embodiments, the one or more cytokines are induced by NF-κB. In some embodiments, antagonizing the STING pathway in a subject comprises reducing expression of one or more of TOR1B, C1orf29, FAM3B, OAS3, USP18, OAS1, Siglec-1, GBP5, IFIT5, IFIT2, IFRG28, IFIT1, PRKR (EIF2AK1), IL1RN, OASL, OAS1, LGALS3BP, OASL, IFIH1 (MDA5), ZBP1, C1QB, CEB1, GBP1, BST2, IFI44, IFI27, GBP2, EPSTI1, CARD15, IFI35, SOCS1, TAP1, XAF1, SP110, OAS2, STAT1, ABCA1, IFIT4, PLSCR1, Cig5, ISG95, STAT2, RIG-I (DDX58), MX2, LGP2, IRF7, ADD45B, SCOTIN, PARP9 (BAL), MT2A, NT5C3 (PN-1), MX1, STAT1, ADAR, TRIM22, G1P2, SERPING1, STAT1, NUB1 (NYREN18), ISG20, LY6E, G1P3, and/or IFITM1 in the subject. In some embodiments, antagonizing the STING pathway in a subject comprises reducing expression of one or more of CCL5, HIF1z, CXCL10, Clorf29, GMPR, IL-6, OAS, IFITM1, TOR1B, OAS1, IFI138, FAM3B, GBP5, IF144L, USP18, IFIT2, PLSCR1, Siglec-1, EPSTI1, TMEM255A, IFIT5, IFI35, SNRPE, IFRG28, TAP1, SNRPA1, PRKR (EIF2AK1), OASL, SNRPB, OASL, ZBP1, SNRPB2, LGALS3BP, CEB1SNRPC, MDA5, BST2, SNRPE, C1QB, IFI2, SNRPF, LGALS3BP, SP110, IRF1, GBP1, STAT1, IRF2, IFI44, IFIT4, Tnfa, GBP2, Cig5, GM-CSF, CARD15, STAT2, IL-13, SOSCS1, MX2, IL-10, XAF1, IRF7, ddx41, OAS2, COTIN, DAI, ABCA1, MT2A, MRE11, PLSCR1, MX1, ISG95, ADAR, RIG-I (DDX58), GIP2, LGP2, LY6E, GADD45B, LAMP3, PARP9 (BAL), CCL2, NT5C3, IF127, STAT1, HSPA1A, TRIM22, HSPA1B, SERPING1, HAPA2, and/or NUB1.

In some embodiments, antagonizing the STING pathway in a subject comprises reducing expression of one or more of STAT1, STAT2, Cig5, G1P3, IRF7, IFIT4, Ly6E, MX1, OAS3 and/or IFI27 in the subject. In some embodiments, the one or more cytokines are induced by IRF3 and NF-κB. In some embodiments, antagonizing the STING pathway in a subject comprises reducing anti-DNA antibody production.

Some embodiments provide a method of treating a viral infection, comprising administering a therapeutically effective amount of a compound of Formula (I), or a pharmaceutically acceptable salt thereof, to a subject in need thereof. Some embodiments provide a method of treating a viral infection comprising administering a therapeutically effective amount of a compound of Formula (II), or a pharmaceutically acceptable salt thereof. In some embodiments, the virus is a DNA virus. In some embodiments, the virus is an RNA virus. In some embodiments, the virus is a coronavirus, such as SARS-Cov2.

Some embodiments provide a method of treating cancer, comprising administering a therapeutically effective amount of a compound of Formula (I), or a pharmaceutically acceptable salt thereof, to a subject in need thereof. Some embodiments provide a method of treating cancer comprising administering a therapeutically effective amount of a compound of Formula (II), or a pharmaceutically acceptable salt thereof.

In some embodiments the cancer is a solid tumor. Non-limiting examples of solid tumors include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In other embodiments, the cancer is a blood cancer. Non-limiting examples of blood cancers include leukemia, myeloma, and lymphoma.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the subject is a human.

In some embodiments, treating the cancer comprises agonizing or partially agonizing STING. In some embodiments, treating the cancer comprises increasing production of IFN-β in the subject. In some embodiments, treating the cancer comprises activating or increasing T-cell immunity. In some embodiments, treating the cancer comprises activating or increasing $CD8^+$ T-cell immunity. In some embodiments, treating the cancer comprises activating or increasing tumor antigen-specific $CD8^+$ T-cell immunity. In some embodiments, increasing T-cell immunity comprises increasing T-cell population.

In the field of medical oncology it is normal practice to use a combination of different forms of treatment to treat each subject with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula (I) and/or Formula (II), or a pharmaceutically acceptable salt thereof therefore may also be useful as adjuvants to cancer treatment, that is, they can be used in combination with one or more additional therapies or therapeutic agents, for example, a chemotherapeutic agent that works by the same or by a different mechanism of action. In some embodiments, a compound of Formula (I) and/or Formula (II), or a pharmaceutically acceptable salt thereof, can be used prior to administration of an additional therapeutic agent or additional therapy. For example, a subject in need thereof can be administered one or more doses of a compound of Formula (I) and/or Formula (II), or a pharmaceutically acceptable salt thereof for a period of time and then undergo at least partial resection of the tumor. In some embodiments, the treatment with one or more doses of a compound of Formula (I) and/or Formula (II), or a pharmaceutically acceptable salt thereof reduces the size of the tumor (e.g., the tumor burden) prior to the at least partial resection of the tumor. In some embodiments, a subject in need thereof can be administered one or more doses of a compound of Formula (I) and/or Formula (II), or a pharmaceutically acceptable salt thereof for a period of time and under one or more rounds of radiation therapy. In some embodiments, the treatment with one or more doses of a compound of Formula (I) and/or Formula (II), or a pharmaceutically acceptable salt thereof reduces the size of the tumor (e.g., the tumor burden) prior to the one or more rounds of radiation therapy.

In some embodiments of any of the methods described herein, the compound of Formula (I) and/or Formula (II), or a pharmaceutically acceptable salt thereof, is administered in combination with an effective amount of at least one additional therapeutic agent selected from one or more additional therapies or therapeutic (e.g., chemotherapeutic) agents.

Non-limiting examples of additional therapeutic agents include: other STING agonists or partial agonists, kinase inhibitors (e.g., receptor tyrosine kinase-targeted therapeutic agents (e.g., Trk inhibitors or EGFR inhibitors) or multi-kinase inhibitors), signal transduction pathway inhibitors, checkpoint inhibitors, modulators of the apoptosis pathway (e.g., obataclax); cytotoxic chemotherapeutics, angiogenesis-targeted therapies, immune-targeted agents, including immunotherapy, and radiotherapy.

Non-limiting examples of multi-kinase inhibitors include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl) piperazine-1-carbothioamide); apatinib (YN968D1) (N-[4-(1-cyanocyclopentyl)phenyl-2-(4-picolyl)amino-3-Nicotinamide methanesulphonate); cabozantinib (Cometriq XL-184) (N-(4-((6,7-Dimethoxyquinolin-4-yl)oxy)phenyl)-N'-(4-fluorophenyl)cyclopropane-1,1-dicarboxamide); dovitinib (TK1258; GFKI-258; CHIR-258) ((3Z)-4-amino-5-fluoro-3-[5-(4-methylpiperazin-1-yl)-1,3-dihydrobenzimidazol-2-ylidene]quinolin-2-one); famitinib (5-[2-(diethylamino)ethyl]-2-[(Z)-(5-fluoro-2-oxo-1H-indol-3-ylidene) methyl]-3-methyl-6,7-dihydro-1H-pyrrolo[3,2-c]pyridin-4-one); fedratinib (SAR302503, TG101348) (N-(2-Methyl-2-propanyl)-3-f{[5-methyl-2-({4-[2-(1-pyrrolidinyl)ethoxy] phenyl}amino)-4-pyrimidinyl] amino}benzenesulfonamide); foretinib (XL880, EXEL- 2880, GSK1363089, GSK089) (N1'-[3-fluoro-4-[[6-methoxy-7-(3-morpholinopropoxy)-4-quinolyl]oxy]phenyl]-N1-(4-fluorophenyl)cyclopropane-1,1-dicarboxamide); fostamantinib (R788) (2H-Pyrido[3,2-b]-1,4-oxazin-3(4H)-one, 6-[[5-fluoro-2-[(3,4,5-trimethoxyphenyl)amino]-4-pyrimidinyl]amino]-2,2-dimethyl-4-[(phosphonooxy) methyl]-, sodium salt (1:2)); ilorasertib (ABT-348) (1-(4-(4-amino-7-(1-(2-hydroxyethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methylamino)-anilino)-1-phenyl-methylene]-6-methyoxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl)phenyl]benzamide); PP242 (torkinib) (2-[4-Amino-1-(1-methylethyl)-1H-pyrazolo[3,4-d]pyrimidin-3-yl]-1H-indol-5-ol); quizartinib (1-(5-(tert-Butyl)isoxazol-3-yl)-3-(4-(7-(2-morpholinoethoxy)benzo[d]imidazo[2,1-b] thiazol-2-yl)phenyl)urea); regorafenib (BAY 73-4506, stivarga) (4-[4-({[4-Chloro-3-(trifluoromethyl)phenyl] carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCD516, MG516) (N-(3-Fluoro-4-{[2-(5-{[(2-methoxyethyl)amino]methyl}-2-pyridinyl)thieno[3,2-b] pyridin-7-yl]oxy}phenyl)-N'-(4-fluorophenyl)-1,1-cyclopropanedicarboxamide); sorafenib (BAY 43-9006) (4-[4-[[[[4-chloro-3-(trifluoromethyl)phenyl]amino]carbonyl] amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl) methyl)-3-(trifluoromethyl)phenyl)carbamoyl)-2-methylphenyl)-5-(thiophen-2-yl)nicotinamide); BPRIK871 (1-(3-chlorophenyl)-3-(5-(2-((7-(3-(dimethylamino) propoxy)quinazolin-4-yl)amino)ethyl)thiazol-2-yl)urea); CLM3 (1-phenethyl-N-(1-phenylethyl)-1H-pyrazolo[3,4-d] pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl) phenyl]-N'-[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methylsulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl) phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl) phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinb (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-di-one); XL-999 ((Z)-5-((1-ethylpiperidin-4-yl)amino)-3-((3-fluorophenyl) (5-methyl-1H-imidazol-2-yl)methylene)indolin-2-one); BPR1J373 (a 5-phenylthiazol-2-ylamine-pyriminide derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD15-44 (N-(4-((4-ethylpiperazin-1-yl)methyl)-3-(trifluoromethyl)phenyl)-4-methyl-3-(pyridin-3-ylethynyl)benzamide (generated from structure)); Y078-DM1 (an antibody drug conjugate composed of a CDC7 antibody (Y078) linked to a derivative of the cytotoxic agent maytansine); Y078-DM4 (an antibody drug conjugate composed of a CDC7 antibody (Y078) linked to a derivative of the cytotoxic agent maytansine); ITRI-305 (DON5 TB, DIB003599); BLU-667 ((1S,4R)-N-((S)-1-(6-(4-fluoro-1H-pyrazol-1-yl)pyridin-3-yl)ethyl)-1-methoxy-4-(4-methyl-6-((5-methyl-1H-pyrazol-3-yl) amino)pyrimidin-2-yl)cyclohexane-1-carboxamide); BLU6864; DS-5010; GSK3179106; GSK3352589; NMS-E668; TAS0286/HM05; TPX0046; and N-(3-(2-(dimethylamino)ethoxy)-5-(trifluoromethyl)phenyl)-2-(4-(4-ethoxy-6-oxo-1,6-dihydropyridin-3-yl)-2-fluorophenyl)acetamide.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö6976, GNF-5837, GTx-186, GW 441756, LOXO-101, MGCD516, PLX7486, RXDX101, VM-902A, TPX-0005, TSR-011, GNF-4256, N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea, AZ623, AZ64, (S)-5-Chloro-N2-(1-(5-fluoropyridin-2-yl)ethyl)-N4-(5-isopropoxy-1H-pyrazol-3-yl)pyrimidine-2,4-diamine, AZD7451, CEP-751, CT327, sunitinib, GNF-8625, and (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol.

Non-limiting examples of a BRAF inhibitor include dabrafenib, vemurafenib (also called RG7204 or PLX4032), sorafenib tosylate, PLX-4720, GDC-0879, BMS-908662 (Bristol-Meyers Squibb), LGX818 (Novartis), PLX3603 (Hofmann-LaRoche), RAF265 (Novartis), RO5185426 (Hofmann-LaRoche), and GSK2118436 (GlaxoSmithKline). Additional examples of a BRAF inhibitor are known in the art.

In some embodiments, the receptor tyrosine kinase inhibitor is an epidermal growth factor receptor typrosine kinase inhibitor (EGFR). For example, EGFR inhibitors can include osimertinib (merelectinib, Tagrisso), erlotinib (Tarceva), gefitinib (Iressa), cetuximab (Erbitux), necitumumab (Portrazza), neratinib (Nerlynx), lapatinib (Tykerb), panitumumab (Vectibix), and vandetanib (Caprelsa).

In some embodiments, signal transduction pathway inhibitors include Ras-Raf-MEK-ERK pathway inhibitors (e.g., binimetinib, selumetinib, encorafenib, sorafenib, trametinib, and vemurafenib), PI3K-Akt-mTOR-S6K pathway inhibitors (e.g., everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

In some embodiments, an additional therapy or therapeutic agent can include a histidyl-tRNA synthetase (HRS) polypeptide or an expressible nucleotide that encodes the HRS polypeptide.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is *bacillus* Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9@ or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; WO 2016/075224; WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Provided herein are methods of treating a subject having a cancer (e.g., any of the cancers described herein) and previously administered a multi-kinase inhibitor (MKI) or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) that include: administering to the subject (i) an effective dose of a compound of Formula (I) and/or Formula (II), or a pharmaceutically acceptable salt thereof as a monotherapy, or (ii) an effective dose of a compound of Formula (I) and/or Formula (II), or a pharmaceutically acceptable salt thereof, and an effective dose of the previously administered MKI or the previously administered target-specific kinase inhibitor.

Also provided herein is a method of inhibiting mammalian cell proliferation, in vitro or in vivo, the method comprising contacting a mammalian cell with an effective amount of a compound of Formula (I) and/or Formula (II), or a pharmaceutically acceptable salt thereof, or a pharmaceutical composition thereof as defined herein.

Some embodiments provide a method of treating an autoimmune disorder in a subject in need thereof, comprising administering a therapeutically effective amount of a compound of Formula (I), or a pharmaceutically acceptable salt thereof, to a subject in need thereof. Some embodiments provide a method of treating an autoimmune disorder comprising administering a therapeutically effective amount of a compound of Formula (II), or a pharmaceutically acceptable salt thereof, to a subject in need thereof. In some embodiments, the autoimmune disorder is selected from SLE, type 1 diabetes, rheumatoid arthritis, psoriatic arthritis, psoriasis, multiple sclerosis, inflammatory bowel disease (e.g., Crohn's disease or ulcerative colitis), Addison's disease, Graves' disease, Sjogren's syndrome, thyroiditis (e.g., Hashimoto's thyroiditis), Myasthenia gravis, autoimmune vasculitis, pernicious anemia, or celiac disease. In some embodiments, the autoimmune disorder is SLE. In some embodiments, treating SLE comprises treating joint pain, heart disease, kidney disease, and photosensitivity in the subject. In some embodiments, treating the autoimmune disorder comprises antagonizing STING, as described herein. In some embodiments, treating the autoimmune disorder comprises reducing expression of IFN-β in the subject, as described herein. In some embodiments, treating the autoimmune disorder comprises reducing expression of one or more cytokines (e.g., two or more, five or more, ten or more, for example up to twenty or fifty cytokines. In some embodiments, the one or more cytokines are induced by IRF3. In some embodiments, the one or more cytokines are induced by NF-κB. In some embodiments, the one or more cytokines are induced by IRF3 and NF-κB. In some embodiments, treating the subject comprises reducing expression of STAT1, STAT2, Cig5, G1P3, IRF7, IFIT4, Ly6E, MX1, OAS3 and IFI27 in the subject. In some embodiments, treating the subject comprises reducing expression of TOR1B, C1orf29, FAM3B, OAS3, USP18, OAS1, Siglec-1, GBP5, IFIT5, IFIT2, IFRG28, IFIT1, PRKR (EIF2AK1), IL1RN, OASL, OAS1, LGALS3BP, OASL, IFIH1 (MDA5), ZBP1, C1QB, CEB1, GBP1, BST2, IFI44, IFI27, GBP2, EPSTI1, CARD15, IFI35, SOCS1, TAP1, XAF1, SP110, OAS2, STAT1, ABCA1, IFIT4, PLSCR1, Cig5, ISG95, STAT2, RIG-I (DDX58), MX2, LGP2, IRF7, ADD45B, SCOTIN, PARP9 (BAL), MT2A, NT5C3 (PN-1), MX1, STAT1, ADAR, TRIM22, G1P2, SERPING1, STAT1, NUB1 (NYREN18), ISG20, LY6E, G1P3, and/or IFITM1 in the subject. In some embodiments, treating the subject comprises reducing expression of STAT1, STAT2, Cig5, G1P3, IRF7, IFIT4, Ly6E, MX1, OAS3 and/or IFI27 in the subject.

In some embodiments, treating the autoimmune disorder comprises reducing anti-DNA antibody production. In some embodiments, anti-DNA antibody production is reduced by about 10% to about 99%, for example, about 10% to about 40%, about 25% to about 50%, about 35% to about 75%, about 50% to about 80%, or about 70% to about 99%. In some embodiments, anti-DNA antibody production is reduced by about 10%, about 20%, about 30%, about 40%, about 50%, about 60%, about 70%, about 80%, about 90%, or about 99%.

In some embodiments, treating the autoimmune disorder comprises reducing inflammation in the subject. In some embodiments, the inflammation is reduced by about about 10% to about 99%, for example, about 10% to about 40%, about 25% to about 50%, about 35% to about 75%, about 50% to about 80%, or about 70% to about 99%. In some embodiments, inflammation is reduced by about 10%, about 20%, about 30%, about 40%, about 50%, about 60%, about 70%, about 80%, about 90%, or about 99%. In some embodiments, the reduction in inflammation is determined by measuring one or more biomarkers associated with inflammation. See, e.g., Brenner, et al., Cancer Epidemiol Biomarkers Prev. 2014 September; 23(9): 1729-1751; Zakynthinos and Pappa, J. Cardiol., 53(3), 317-333 (2009); Liu, et al., Nat. Immunol., 18; 1175-1180 (2017); Roemer, et al., Arthrit. Rheum. 71(2) 238-243 (2019), each of which is incorporated by reference in its entirety.

In some embodiments, the subject also has a mutation in the TREX1 gene. In some embodiments, the autoimmune disorder is associated with the mutation in the TREX1 gene in the subject.

It is normal practice to use a combination of different forms of treatment to treat a subject with an autoimmune disorder. The other component(s) of such conjoint treatment or therapy in addition to compositions provided herein (e.g., the compounds of Formula (I) and/or (II) or pharmaceutically acceptable salts thereof) may be, for example, anti-inflammatory drugs, cytotoxic chemotherapeutic drugs, immunosuppressants, kidney support, anti-rheumatic drugs, monoclonal antibodies, and avoiding sun exposure.

In some embodiments of any of the methods described herein, the compound of Formula (I) and/or Formula (II), or a pharmaceutically acceptable salt thereof, is administered in combination with an effective amount of at least one anti-inflammatory drug selected from steroids (e.g., corticosteroids, hydrocortisone, prednisone, triamcinolone, betamethasone, dexamethasone, Prednisolone, methylprednisolone), ibuprofen, naproxen, aspirin, diclofenac, meloxicam, and tolmetin. The at least one anti-inflammatory drug may be a topical drug or treatment. Topical drugs or treatments include, but are not limited to, triamcinolone and fluocinolone.

In some embodiments of any of the methods described herein, the compound of Formula (I) and/or Formula (II), or a pharmaceutically acceptable salt thereof, is administered in combination with an effective amount of at least one cytotoxic chemotherapeutic drug selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In some embodiments of any of the methods described herein, the compound of Formula (I) and/or Formula (II), or a pharmaceutically acceptable salt thereof, is administered in combination with an effective amount of at least one immunosuppressant selected from azathioprine, methotrexate, mycophenolate, imuran, azathioprine, Mycophenolate mofetil, Tacrolimus, Sirolimus, Everolimus, and Interferons.

In some embodiments of any of the methods described herein, the compound of Formula (I) and/or Formula (II), or a pharmaceutically acceptable salt thereof, is administered in combination with an effective amount of at least one anti-rheumatic drug selected from hydroxychloroquine, celecoxib, abatacept, adalimumab, anakinra, apremilast, baricitinib, certolizumab pegol, ciclosporin (Cyclosporin A), D-penicillamine, etanercept, filgotinib, golimumab, infliximab, leflunomide, methotrexate, minocycline, rituximab, sarilumab, secukinumab, sulfasalazine, tocilizumab, tofacitinib, and ustekinumab.

In some embodiments of any of the methods described herein, the compound of Formula (I) and/or Formula (II), or a pharmaceutically acceptable salt thereof, is administered in combination with an effective amount of at least one monoclonal antibody selected from abciximab, alefacept, alemtuzumab, basiliximab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, tocilizumab, trastuzumab, secukinumab, ustekinumab, belimumab, rituximab, infliximab, and adalimumab.

Pharmaceutical Compositions

When employed as pharmaceuticals, compounds of Formula (I) and/or Formula (II), including pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intra-peritoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula (I) and/or Formula (II) or pharmaceutically acceptable salt thereof, in combination with one or more pharmaceutically acceptable excipients. For example, a pharmaceutical composition prepared using a compound of Formula (I) and/or Formula (II) or a pharmaceutically acceptable salt thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula (I) and/or Formula (II) or a pharmaceutically acceptable salt thereof with a pharmaceutically acceptable carrier. Pharmaceutical compositions containing a compound of Formula (I) and/or Formula (II) or a pharmaceutically acceptable salt thereof as the active ingredient can be prepared by intimately mixing the compound of Formula (I) and/or Formula (II), or a pharmaceutically acceptable salt thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing the compositions in oral dosage form, any of the usual pharmaceutical media can be employed. Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver an effective dose as described herein.

The compositions comprising a compound of Formula (I) and/or Formula (II), or a pharmaceutically acceptable salt thereof, can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other subjects, each unit containing a predetermined quantity of active material (i.e., a compound of Formula (I) and/or Formula (II) or a pharmaceutically acceptable salt thereof) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain about 10 mg, about 20 mg, about 80 mg, or about 160 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The daily dosage of the compound of Formula (I) and/or Formula (II) or a pharmaceutically acceptable salt thereof can be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 160, 200, 250 and 500 milligrams of the active ingredient for the symptomatic adjustment of the dosage to the subject to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. Pharmaceutical compositions containing a compound of Formula (I) and/or Formula (II) or a pharmaceutically acceptable salt thereof can be administered on a regimen of 1 to 4 times per day or in a single daily dose.

Some embodiments provide a method of treating Aicardi-Goutieres Syndrome comprising administering a therapeutically effective amount of a compound of Formula (I) and/or Formula (II), or a pharmaceutically acceptable salt thereof, to a subject in need thereof. In some embodiments, the subject also has a mutation in the TREX1 gene. In some embodiments, the Aicardi-Goutieres Syndrome is associated with the mutation in the TREX1 gene in the subject.

Some embodiments provide a method of treating embryonic lethality polyarthritis comprising administering a therapeutically effective amount of a compound of Formula (I) and/or Formula (II), or a pharmaceutically acceptable salt thereof, to a subject in need thereof. In some embodiments, the subject has a Dnase II genetic deficiency. In some embodiments, the embryonic lethality polyarthritis is associated with a Dnase II genetic deficiency in the subject.

Some embodiments provide a method of treating Type I interferon perinatal lethality comprising administering a therapeutically effective amount of a compound of Formula (I) and/or Formula (II), or a pharmaceutically acceptable salt thereof, to a subject in need thereof. In some embodiments, the subject has a genetic deficiency in RNaseH2. In some embodiments, the Type I interferon perinatal lethality is associated with a genetic deficiency in RNaseH2 in the subject.

Some embodiments provide a method of treating inflammation comprising administering a therapeutically effective amount of a compound of Formula (I) and/or Formula (II), or a pharmaceutically acceptable salt thereof, to a subject in need thereof.

Some embodiments provide a method of treating inflammaging comprising administering a therapeutically effective amount of a compound of Formula (I) and/or Formula (II), or a pharmaceutically acceptable salt thereof, to a subject in need thereof.

Some embodiments provide a method of treating a viral infection comprising administering a therapeutically effective amount of a compound of Formula (I) and/or Formula (II), or a pharmaceutically acceptable salt thereof, to a subject in need thereof. In some embodiments, the viral infection is caused by a DNA or RNA virus. In some embodiments, the viral infection is caused by a DNA virus. In some embodiments, the viral infection is caused by an RNA virus. In some embodiments, the viral infection is caused by a coronavirus. In some embodiments, the viral infection is caused by SARS-CoV-2.

The active compound may be effective over a wide dosage range and is generally administered in a pharmaceutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular subject being treated, including subject response, age, weight, diet, time of administration and severity of the subject's symptoms, will result in the need to adjust dosages.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

In some embodiments, the compounds provided herein can be administered in an amount of about 10 mg twice a day (BID), 20 mg BID, about 40 mg BID, about 60 mg BID, about 80 mg BID, about 120 mg BID, about 160 mg BID, and about 240 mg BID. In some embodiments, each dose is administered at least six hours after the previous dose. In some embodiments, each dose is administered at least twelve hours after the previous dose.

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, can be completed according to methods well known in the clinical and medical arts.

Provided herein are pharmaceutical kits useful, for example, in the treatment of STING-associated diseases or disorders, such as cancer, which include one or more containers containing a pharmaceutical composition comprising an effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Definitions

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The term "pharmaceutically acceptable salt" indicates that the salt is compatible chemically and/or toxicologically with the other ingredients comprising a formulation and/or the subject being treated therewith.

The term "partial agonist" or "partially agonizing", as used herein, refers to a property of a compound to bind to and activate a given receptor or protein (e.g., STING), but have partial efficacy or activity at the receptor at any concentration relative to a full agonist. In some embodiments, partial agonism of STING may be associated with a net negative effect, resulting in suppression of the STING signal.

The term "full agonist", as used herein, refers to a property of a compound to bind to and activate a given receptor or protein (e.g., STING), with the maximum response that an agonist can elicit at the receptor (e.g., with the response that an endogenous ligand can elicit at the receptor).

The term "halogen," refers to —F, —Cl, —Br and —I.

The term "pseudohalogen," as used herein, refers to polyatomic analogues of halogens, which possess similar chemistry (e.g., bioisosterism) to halogens. Pseudohalogens include, but are not limited to cyano, isocyano, thiocyano, isothiocyano, —OH, —SH, azide, and trifluoromethanesulfonate.

The term "alkyl" as used herein refers to saturated linear or branched-chain monovalent hydrocarbon radicals of the indicated number of carbon atoms. Alkyl groups can be straight chain or branched. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a C6-C14 aryl group, a C6-C10 aryl group, or a C6 aryl group. Examples of aryl groups include, but are not limited to, benzene, naphthalene, and azulene.

As used herein, "heteroaryl," refers to a monocyclic, bicyclic or tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine.

As used herein, "heterocyclyl" and "heterocycle" refer to three-, four-, five-, six-, seven-, eight-, nine-, ten-, up to 18-membered monocyclic, bicyclic, or tricyclic ring system that is not fully aromatic wherein carbon atoms together with from 1 to 5 heteroatoms constitute said ring system. A heterocycle may optionally contain one or more elements of unsaturation. The heteroatom(s) is an element other than carbon including, but not limited to, oxygen, sulfur, and nitrogen. A heterocycle may further contain one or more carbonyl or thiocarbonyl functionalities, so as to make the definition include oxo-containing systems and thio-containing systems such as lactams, lactones, cyclic imides, cyclic thioimides, and cyclic carbamates. When composed of two or more rings, the rings may be joined together in a fused, bridged, or spirocyclic fashion. Additionally, any nitrogens in a heterocycle may be quaternized. Heterocyclyl groups may be unsubstituted or substituted. Examples of such "heterocyclyl" groups include, but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which interconvert according to, e.g., a facile and rapid equilibrium. It is to be understood that compounds provided herein may be depicted as different tautomers, and when compounds have tautomeric forms, all tautomeric forms are intended to be within the scope of the invention, and the naming of the compounds does not exclude any tautomer.

It will be appreciated that certain compounds provided herein may contain one or more centers of asymmetry and may therefore be prepared and isolated in a mixture of isomers such as a racemic mixture, or in an enantiomerically pure form.

EXAMPLES

Example 1: Compound Preparation

Materials and Methods

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry,* 1$^{st}$ Ed., Oxford University Press, 2000; *March's Advanced Organic Chemistry: Reactions, Mechanisms, and Structure,* 5$^{th}$ Ed., Wiley-Interscience Publication, 2001; and Petursson, S. et al., "*Protecting Groups in Carbohydrate Chemistry,*" *J. Chem. Educ.,* 74(11), 1297 (1997).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874

(2004), normal phase silica chromatography, and supercritical fluid chromatography (SFC).

Exemplary Synthesis of Compounds of Formula (II)

The Scheme below depicts the preparation of compound 1 and compound 2. Intermediate A was coupled with allyl alcohol in the presence of dicyclohexylcarbodiimide (DCC) in dichloromethane to produce the corresponding allyl ester B. Allyl ester B was dimerized via olefin metathesis in the presence of Grubbs-Hoveyda catalyst to generate intermediate C. Intermediate C was then hydrogenated in the presence of a catalyst to produce compound 1, or dihydroxylated to produce compound 2.

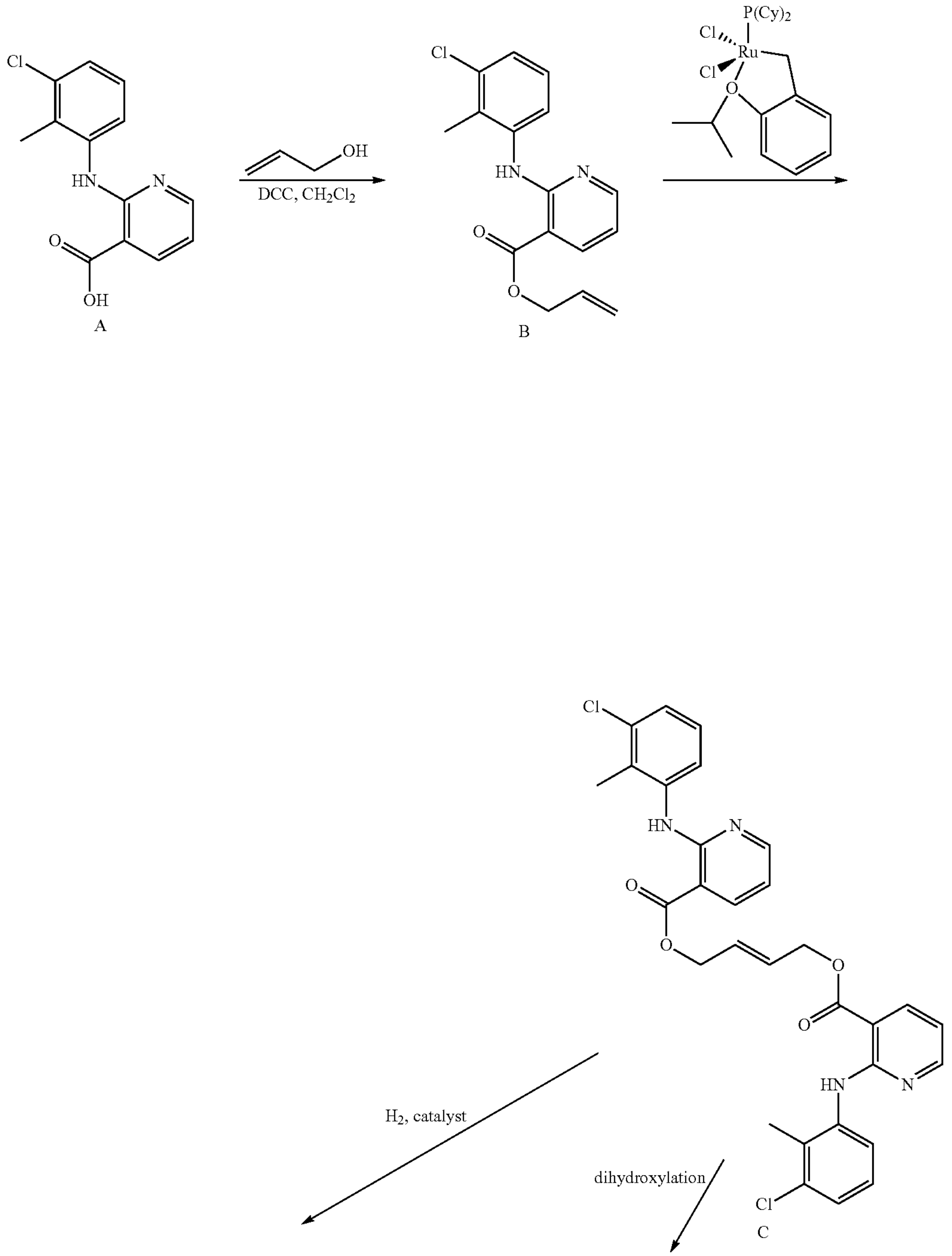

A

B

C

-continued

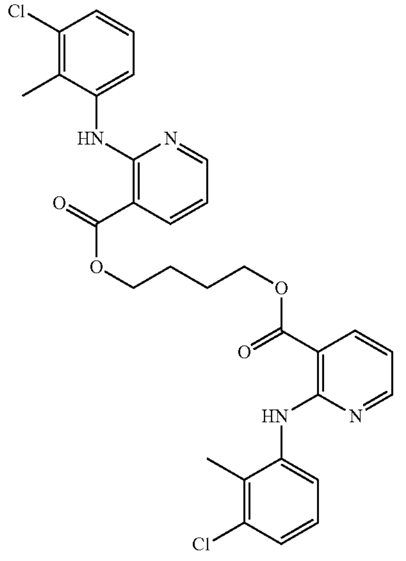

1

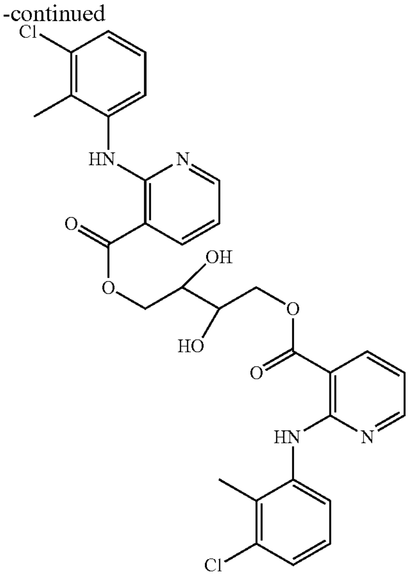

2

The skilled artisan would understand that other catalysts, solvents, temperatures, times, and reagents could be used interchangeably in the process, for example, as needed to address functional group tolerance.

Other compounds of Formula (I) and/or Formula (II) may be prepared using routes analogous to the one shown above.

Example 2: Cellular Assays

NSC335504

A model compound used in certain assays described herein is referred to as NSC335504, whose structure is shown below:

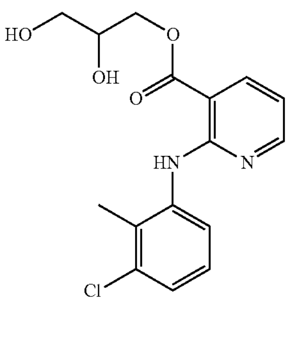 [SMILES: Cc1c(Cl)cccc1Nc1ncccc1C(=O)OCC(O)CO]

FIG. 1 shows the mass spectrum and corresponding peak table of NSC335504.

Cellular Assays

THP1-ISG-Lucia cells were obtained from Invivogen and maintained in RPMI 1640 containing 2 mM L-glutamine, 25 mM HEPES, 10% heat-inactivated fetal bovine serum, 100 μg/ml Normocin™, Pen-Strep (100 μg/ml). To maintain selection pressure, 10 μg/ml of blasticidin and 100 μg/ml of Zeocin™ was added to the growth medium every other passage.

Reporter cells were plated at 100,000 (THP1-ISG-Lucia) cells per well in a white 300 uL sterile 96 well plate and treated with 3, 5, 10, 15, 20, 30, 40, 50 μM 2,3-cGAMP, DMSO and NSC 335504. For compounds, 10 mM stock solution in 100% DMSO was diluted 1:4 with ultrapure Milli Q water. For the positive control, 1 mM stock solution in 100% Milli Q $H_2O$ was diluted 3:1 with water. 50 μL of QUANTI-Luc™ luminesence assay reagent (Invivogen) was added after 18-24 h incubation period. Expression of Lucia luciferase was quantified by measuring luminescence from duplicate treatments. Data illustrated were average luminescence changes shown relative to DMSO-treated cells.

THP1-Dual KI-hSTING-R232 Cells from Invivogen contain a knockin of the intronless coding sequence of the R232 hSTING variant. This variant, which contains an arginine at position 232 (R232), is the most prevalent variant (~45-58%) in the human population. This isoform is preferentially activated by 2'5'linkage-containing cGAMP isomers.

Western Blot:

Cell extracts were prepared after the addition of cell lysis buffer, sonication, and centrifugation (at 12,879×g for 15 min at 4 °C). For western blot analysis, 20 μg of protein from cell lysates was loaded in 10% polyacrylamide gels and separated by using sodium dodecyl sulfate-polyacrylamide gel electrophoresis (SDS-PAGE). The proteins were then transblotted onto a 0.4 μM nitrocellulose membrane. Subsequently, the membranes were incubated with 5% milk blocking solution, followed by primary solution of Phospho-STING (Ser366; #43499; 1:1,000; Cell Signaling Technology, Danvers, MA, USA) in 5% bovine serum albumin (BSA). Finally, the membranes were incubated with secondary antibodies. All the secondary antibodies (anti-rabbit and anti-mouse) were obtained from Bio-Rad Laboratories, Hercules, CA, USA (cat. no. 170-6515 and cat. no. 170-6516; 1:2,000). The immunoreactive bands were then visualized by chemiluminescence reaction, according to the manufacturer's instructions (SuperSignal™ West Pico PLUS Chemiluminescent Substrate; Thermo Fisher Scientific, Inc.). A monoclonal antibody to β-actin (SC-1616; Santa Cruz Biotechnology) was used as a loading control.

Luciferase:

THP1-ISG-Lucia cells were obtained from Invivogen and maintained in RPMI 1640 containing 2 mM L-glutamine, 25 mM HEPES, 10% heat-inactivated fetal bovine serum, 100

μg/ml Normocin™, Pen-Strep (100 μg/ml). To maintain selection pressure, 10 μg/ml of blasticidin and 100 μg/ml of Zeocin™ was added to the growth medium every other passage.

Reporter cells were plated at 100,000 (THP1-ISG-Lucia) cells per well in a white 300 uL sterile 96 well plate and treated with 3, 5, 10, 15, 20, 30, 40, 50 μM 2,3-cGAMP, DMSO and NSC 335504. For compounds, 10 mM stock solution in 100% DMSO was diluted 1:4 with ultrapure Milli Q water. For the positive control, 1 mM stock solution in 100% Milli Q $H_2O$ was diluted 3:1 with water. 50 μL of QUANTI-Luc™ luminesence assay reagent (Invivogen, San Diego, CA, USA) was added after 18-24 h incubation period. Expression of Lucia luciferase was quantified by measuring luminescence from duplicate treatments. Data illustrated are average luminescence changes shown relative to DMSO-treated cells. A Glowmax luminometer (Promega, Madison, Wis., USA) was used. QUANTI-Luc™ was prepared following the manufacturer's instructions. 10 μl of THP1-Dual™ KI-hSTING-R232 cell culture supernatant was pipetted into each well in a 96-well white (opaque) plate. 50 μl of QUANTI-Luc™ was added to each well. The measurement was then immediately taken using a 4 sec incubation time and integrating over 1 sec.

THP1-Dual KI-hSTING-R232 Cells from Invivogen contain a knockin of the intronless coding sequence of the R232 hSTING variant. This variant, which contains an arginine at position 232 (R232), is the most prevalent variant (~45-58%) in the human population. This isoform is preferentially activated by 2'5' linkage-containing cGAMP isomers.

Surface Plasmon Resonance (SPR)

SPR was employed for binding measurements using His-tagged human STING CDN domain. A GE Healthcare Biacore T200 was equipped with an Ni-NTA chip. 16,951 RU of 6×-His tagged human STING was crosslinked via NHS chemistry following injections of 350 mM EDTA and 500 mM NiSO4. STING natural substrates and the lead compound were titrated and flowed at 60 uL/min in 1×PBS for 60 sec association time followed by a 135 sec dissociation. The sensorgrams were analyzed using Biacore T200 Software 3.0 (GE Healthcare) and steady state was measured at 4 sec before injection stop, exported into Graphpad, and fit vs concentration using a one site specific binding model to calculate the apparent equilibrium dissociation constant (KD). Where appropriate, kinetics were measured using a 1:1 Langmuir binding model with Rmax set to local to obtain the association rate (Kon), dissociation (Koff), and the KD.

Cellular Assay

Figure 2:
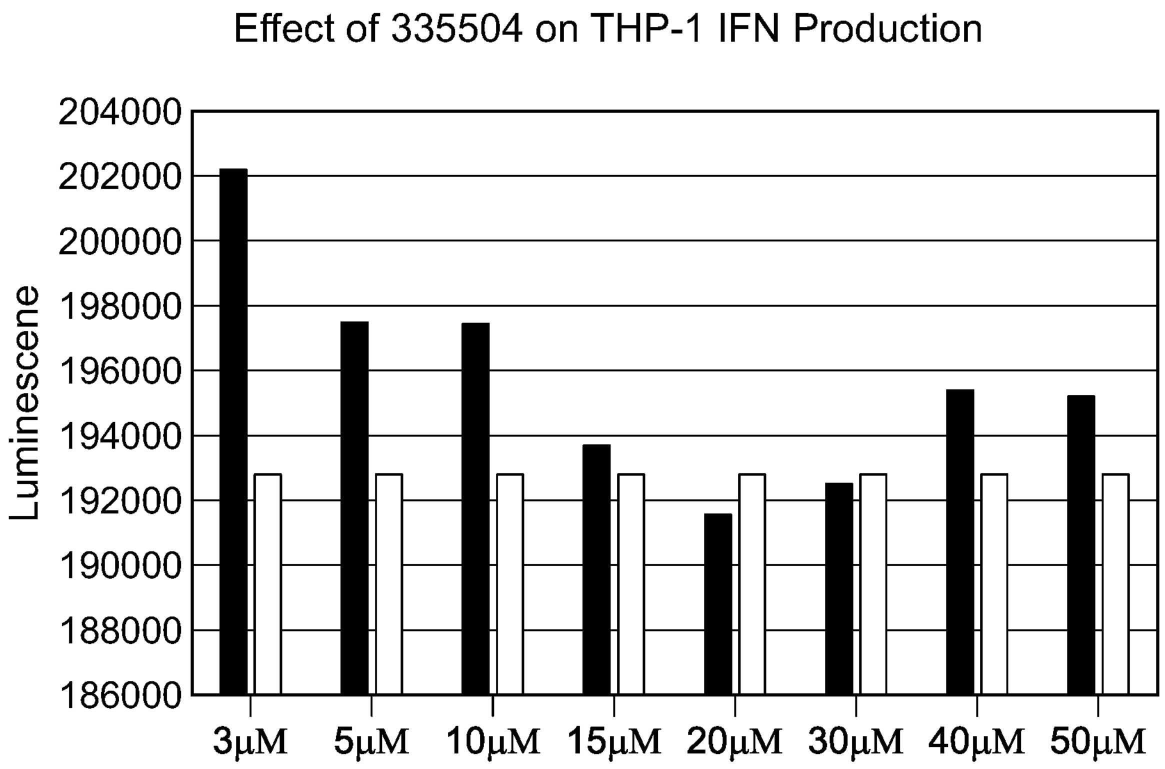
FIG. 2 illustrates luminescence vs. concentration of 335504 compared a DMSO blank in a THP1 luciferase assay.

A luciferase assay utilizing monocytic leukemia THP-1 cells was carried out to determine the upregulation of the IRF3 promoter gene as a downstream indicator of STING pathway activation. 335504 was diluted according to the aforementioned methods. FIG. 2 is a graph showing luminescence vs. concentration of 335504 (left bar in each pair of bars) compared a DMSO blank (right bar in each pair of bars). A significant response to NSC 335504 was observed in comparison to the negative control. At low (3 μM) concentrations, a large increase in ISG output was observed. At higher (>20 μM) concentrations of compound, DMSO percentages increased, hindering the growth of the monocytes and thus decreasing the amount of luminescence observed. Higher concentrations appeared to cause cell death.

MST

Nanotemper Monolith NT.115 labeled thermophoresis machine was used with standard treated capillary tubes using samples comprised of labeled protein and titrations of small molecule in 1×PBS. Microscale thermophoresis (MST) experiments were conducted in triplicate mixing 200 nM protein with 100 nM dye and allowing to sit at room temperature for 30 minutes followed by centrifugation on Ni-NTA 488 labeled His-labeled STING. Detection of the protein was performed using the blue detection channel with LED excitation power set to 90% and MST set to high allowing 3 s prior to MST on to check for initial fluorescence differences, 25 s for thermophoresis, and 3 s for regeneration after MST off. Analysis was performed using M.O. Affinity Analysis Software with difference between initial fluorescence measured in the first 5 s as compared with thermophoresis at 15 s at 15 different analyte concentrations ranging from 15 nM to 1 mM and exported into Graphpad Prism v.8 using a Log inhibitor v. response 4 parameter fit.

Example 3: Computational Modeling (Virtual Screening)

Protein Preparation

Protein model systems hSTING variants were prepared using commercially available software. Protein structure coordinates were downloaded from the Protein Data Bank (PDB). The hSTING models were generated from the PDB entries: 4LOH (REF allele co-crystallized with 23-cGAMP), 4LOI (REF allele co-crystallized with 22-cGAMP), 4EMT (REF allele co-crystallized with c-di-GMP), 4EMU (REF allele apo structure), 4KSY (WT allele co-crystallized with 23-cGAMP), and 4F5W (HAQ allele apo structure). The apo structures for hSTING, PDB 4EMU, were used to cross reference conformational states from MD simulations. PDB systems were prepared with the Protein Preparation Wizard (PrepWizard) in Maestro. Cofactors used in crystallization (such as sulfate or phosphate ions), ligands, and additional protein dimers were deleted. Bond orders were then assigned, including disulfide bridges, and original hydrogens were deleted and later replaced to reduce bad contacts and other crystal artifacts before protonation and hydrogen bond optimization. All waters were retained for assisting in the determination of side chain protonation states and initial hydrogen bond optimization. Missing side chains were added and optimized using Prime. Hydrogen atoms were then added to the protein, remaining cofactors, and to any added structural waters. The program PROPKA was used for the prediction of protein ionization states at 7.4 pH and ProtAssign was used for hydrogen bond optimization. After automatic hydrogen assignment, visual inspection was used to flip residues and change protonation states at protein-protein interfaces if and when appropriate.

Molecular Dynamics

Molecular dynamics (MD) simulations were performed with the GPU accelerated Desmond MD program on two Nvidia GeForce GTX 1080 Ti video cards. A cubic simulation box was created extending at least 10 Å from the protein with imposed periodic boundary conditions using TIP3P waters as solvent. The OPLS-3 all-atom force field was then applied to all atoms. Simulations were run at a temperature of 310 K and a constant pressure of 1 atm. All systems were energy minimized followed by multiple restrained minimizations to randomize systems before equilibration and final simulation. Production MD was performed on all systems for 250 ns.

Final system equilibration is determined by the observation of asymptotic behavior of the potential energy, Root Mean Square Deviation (RMSD), and Radius of Gyration (Rg) profiles and visual inspection of trajectories guided by Root Mean Square Fluctuation (RMSF) profiles.

Consensus Docking

After equilibration is determined, a hierarchical average linkage clustering method based on RMSD was utilized to determine an average representative structure for the equilibrated hSTING systems. The program PROPKA was then implemented again on the equilibrated structure to test consistency of side chain protonation states at 7.4 pH. The representative structure was then used for consensus docking incorporating four diverse and complementary docking methods, SP and XP rigid receptor docking, Induced Fit Docking, and Quantum Polarized Ligand Docking. By applying these varied energy scoring methods, the weaknesses of each method was identified for a particular model and error statistically minimized, yielding a more accurate summary of ligand binding dispositions and affinities.

As a check for the placement of the grids used in the docking studies and for further analysis of the binding cavity for the CDN binding site, Schrödinger's SiteMap program is employed. SiteMap searches the protein structure for likely binding sites and highlights regions within the binding site suitable for occupancy by hydrophobic groups, hydrogen-bond donors, acceptors, or metal-binding functionality of the ligand.

All ligands were prepared using the program LigPrep and the OPLS-3 all-atom force field was applied to all ligand atoms.

Rigid Receptor Docking (RRD)

Rigid docking simulations were performed by the docking program Glide. Glide uses a GlideScore fitness function based on Chemscore for estimating binding affinity, but includes a steric-clash term, adds buried polar terms to penalize electrostatic mismatches, and modifies other secondary terms. Docking simulations used both the standard precision (SP) and extra precision (XP) methods. XP mode is a refinement algorithm enforced only on good ligand poses. Sampling is based on an anchor and refined growth strategy and the scoring function includes a more complete treatment of some of the SP energetic terms, such as the solvation and hydrophobic terms. Docking grids were defined by a rectangular ligand atom inclusion outer box of 22 Å and ligand centroid constraint inner box of 10 Å in the x, y, and z directions originating from the binding cavity centroid defined by SiteMap.

Induced Fit Docking (IFD)

The IFD methodology incorporated both the docking program Glide to account for ligand flexibility and the Refinement module in the Prime program to account for receptor flexibility. The Schrödinger IFD protocol attempts to model induced-fit effects from alterations in binding site conformation due to ligand binding in order to increase accuracy of binding affinity estimates and prediction of possible binding modes.

Separate cubic docking grids for the CDN binding site were centered on the original co-crystallized ligand centroid and from the binding cavity centroids defined by SiteMap. A constrained minimization of the receptor was performed preceding an initial softened potential Glide docking of the ligand set was then implemented with the standard precision (SP) mode. The resulting top 20 poses of the ligands are used to sample protein plasticity by conformational searches and minimizations of binding pocket residues within 6 Å of any ligand pose for all complexes obtained. The new receptor conformations were then redocked using complexes within 30 kcal/mol from the best scoring structure.

The estimated binding affinity of each complex was reported in the GlideScore and used to compare differences between each ligand while the Emodel score is used to inter-compare poses of the ligands. Emodel places more significance on weighting force field components (electrostatic and van der Waals energies), making it better for comparing conformers as opposed to comparing chemically-distinct species.

Quantum Polarized Ligand Docking (QPLD)

To account for ligand polarization upon binding, Quantum Mechanics/Molecular Mechanics (QM/MM) docking was performed by the Schrödinger QM-Polarized Ligand Docking Protocol (QPLD). The protocol first employs RRD using Glide in SP mode. In this step, the top five poses of each ligand in the initial RRD were used. Potential ligand polarization induced by the protein were then calculated with QSite at the B3LYP/6-31G* level. The ligand force fields were then reconstructed with QM/MM modified charges, redocked, and five poses of each ligand were saved for evaluation.

Virtual Target Screening (VTS)

VTS is a system designed to virtually screen a molecule of interest to a large library of protein structures. The current protein library consists of 1,451 structures. The system was calibrated with a set of small drug-like molecules docked against each structure in the protein library to produce benchmark statistics. VTS is employed as a theoretical assay to gauge the potential biological promiscuity. The calibration procedure allows the analysis to accurately predict binding affinities when $Kd<10\ \mu M$ (defining a hit) and $Kd \geq 10\ \mu M$ are both considered (72% accuracy in the best case). Therefore, the VTS system was able to robustly discriminate protein binders from nonbinders and give some inclination as to potential binding promiscuity of the molecule of interest with respect to the protein group tested.

Molecular Mechanics and Generalized Born Surface Area (MM/GBSA)

The MM/GBSA method combined molecular mechanics energy terms and implicit solvation models to calculate the binding-free energy based on docking complexes. The simulation was performed based on receptor-ligand complex structures obtained from IFD. The obtained ligand poses were minimized using the local optimization feature in Prime, whereas the energies of complex were calculated with the OPLS-3 force field and Generalized-Born/Surface Area continuum solvent model. During the simulation process, the ligand strain energy was also considered.

Figure 3A:
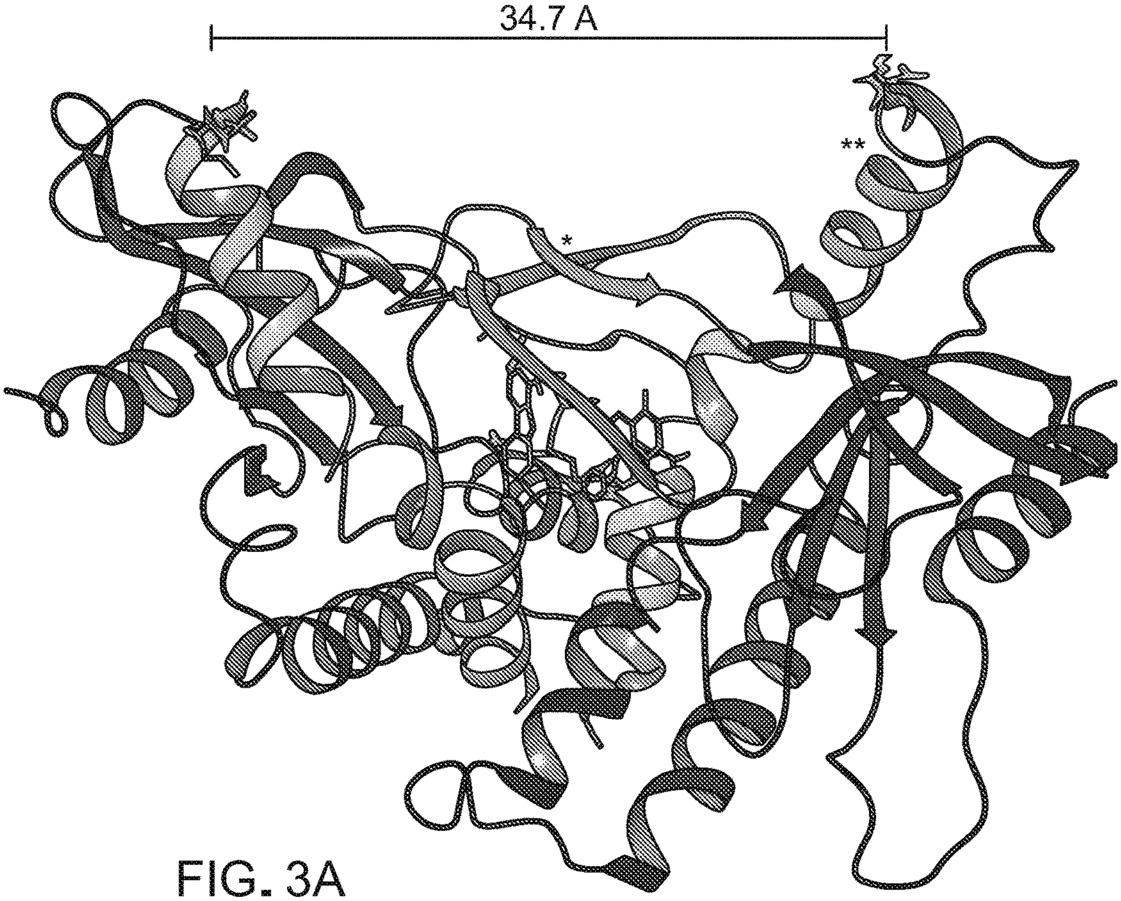
FIG. 3A depicts a holo structure of $hSTING^{REF}$ bound to 23-cGAMP.
Figure 3B:
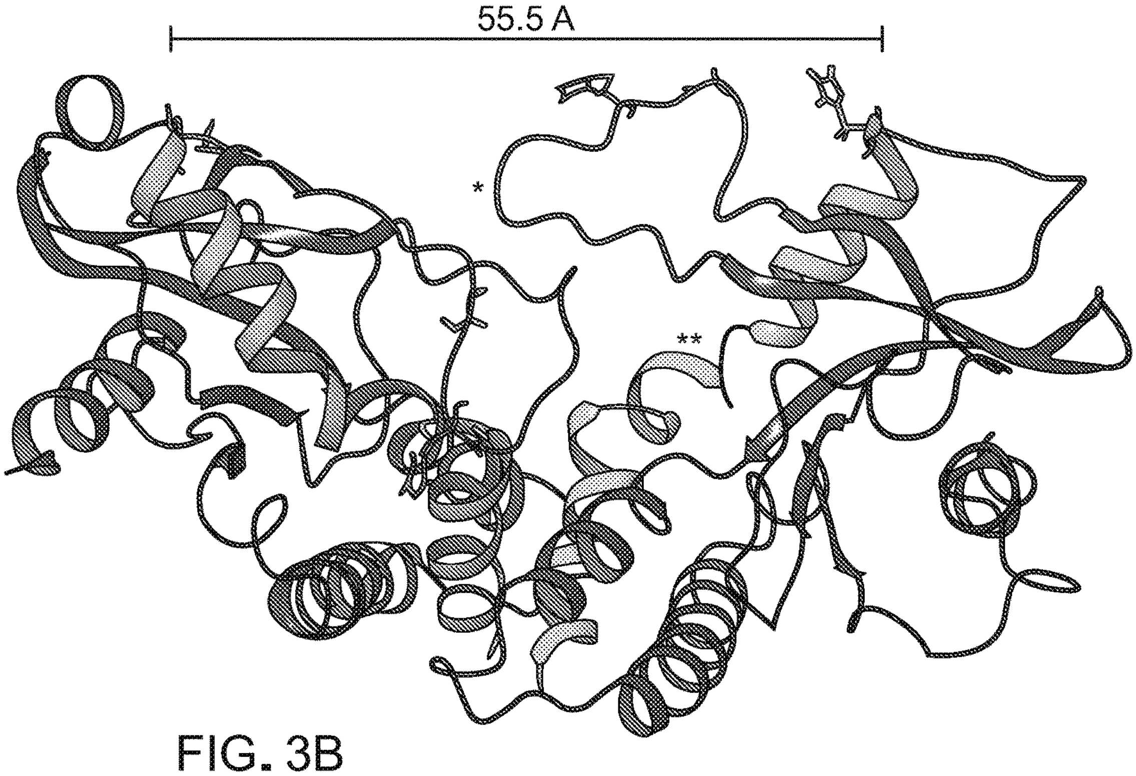
FIG. 3B depicts an apo structure of $hSTING^{REF}$.
Figure 3C:
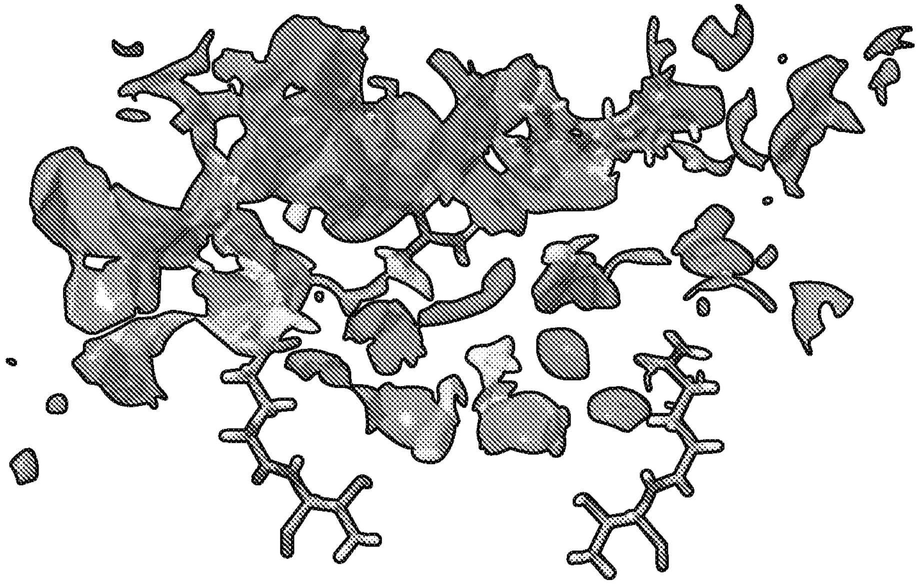
FIG. 3C depicts a SiteMap analysis between CDN binding sites of hSTING.
Figure 3D:
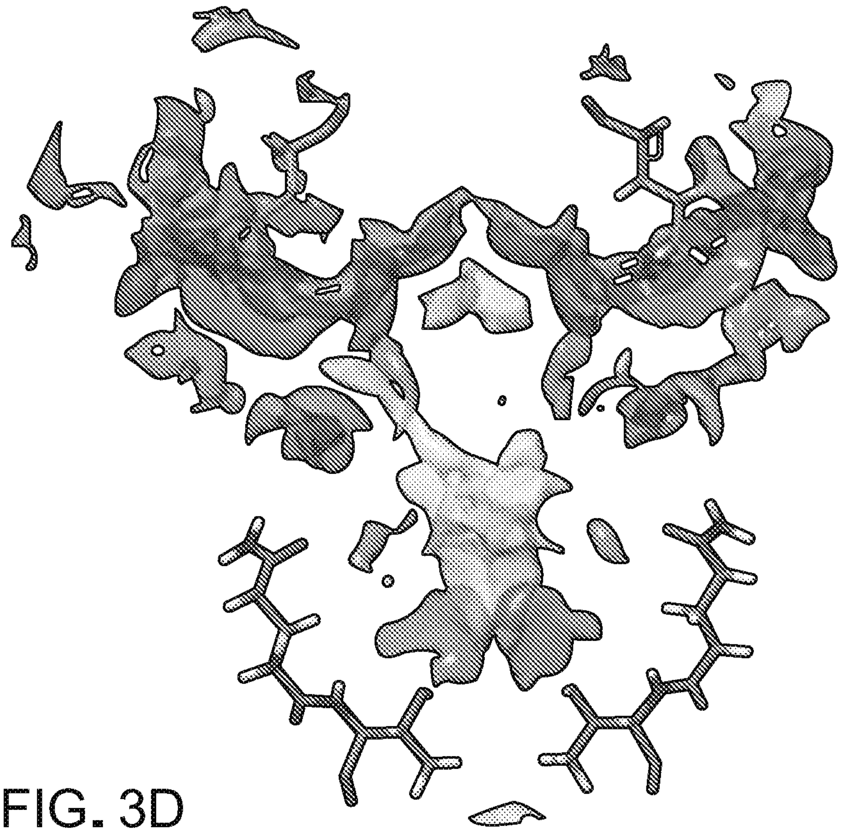
FIG. 3D depicts a SiteMap analysis between CDN binding sites of mSTING.
Figures 3E, 3F:
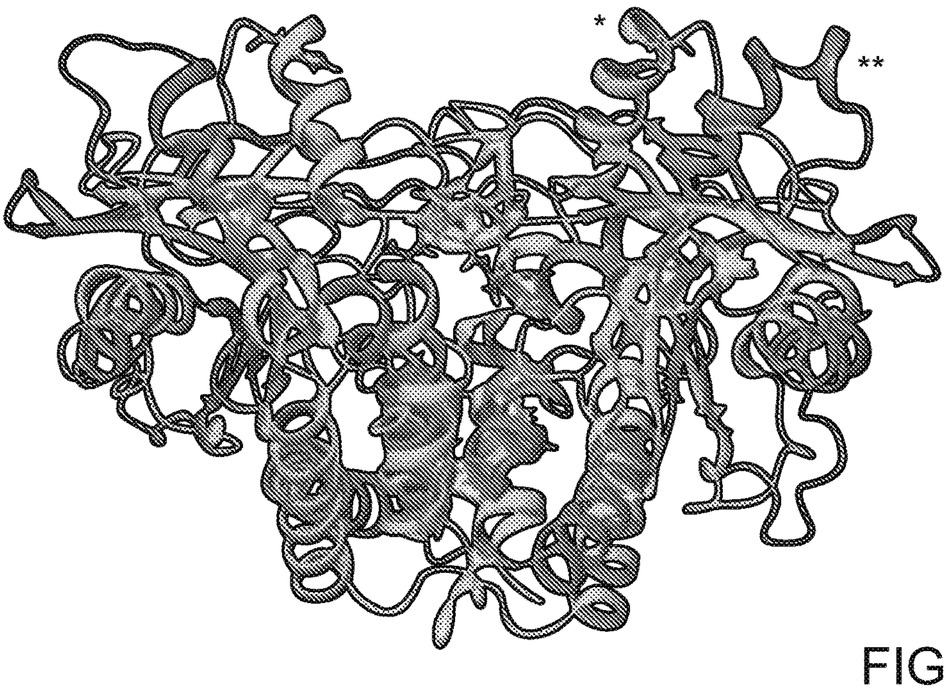
FIG. 3E depicts a ribbon overlay comparing structures of mSTING and hSTING.
FIG. 3F is a table of docking score comparisons.
Figure 3G:
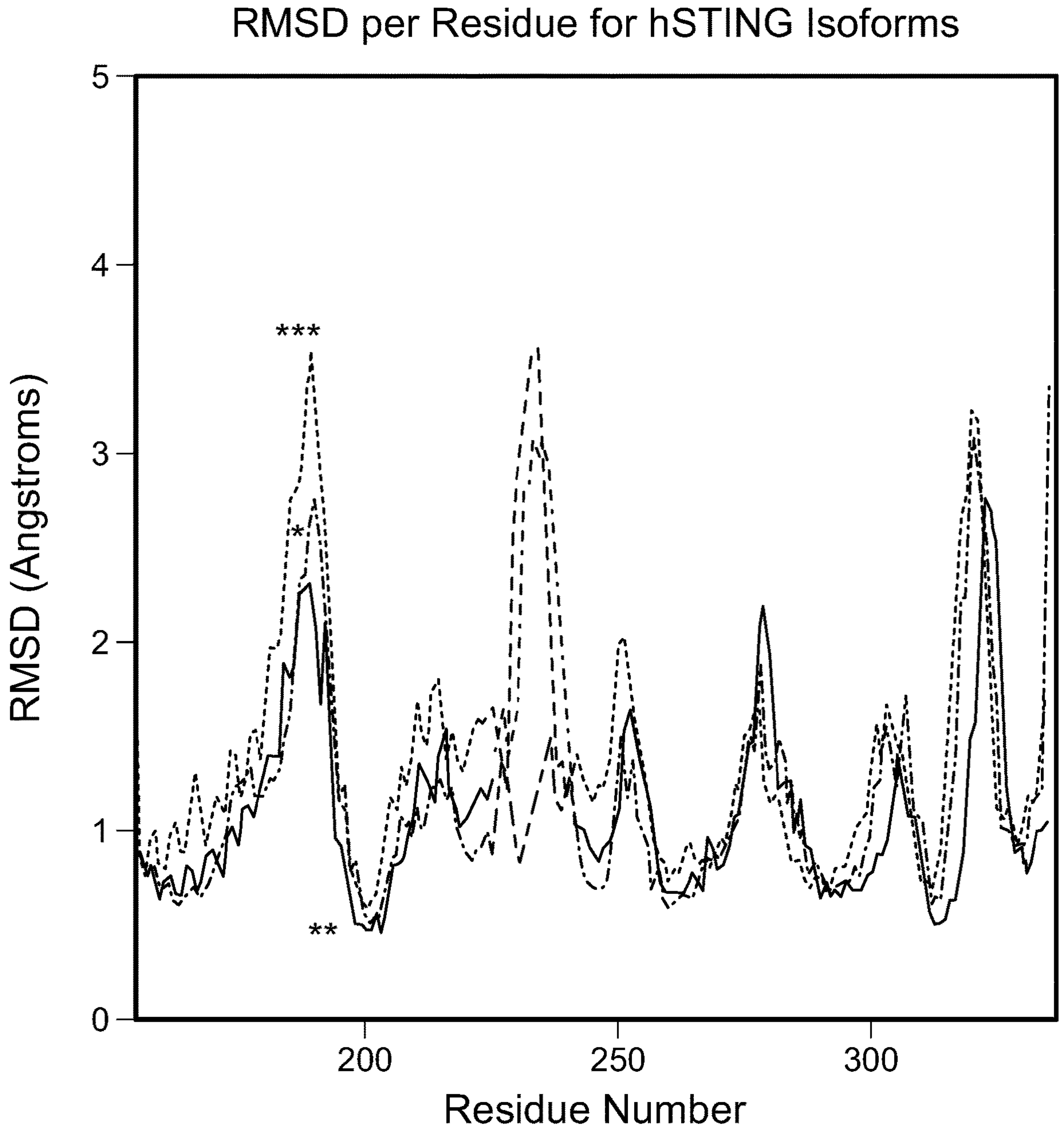
FIG. 3G is a plot of Root Mean Square Fluctuation (RMSF) profiles.

FIGS. 3A-3B depict $hSTING^{REF}$ CTD structures after MD with distance between H185 residue shown for holo structure bound to 23-cGAMP (FIG. 3A) and apo structure (FIG. 3B). "Lid" region demarcated with  and α1 and α2 helix in *. Residues H185, G230, and H232 represented as tubes for clarity. FIGS. 3C-3D depict SiteMap analyses between CDN binding sites of hSTING (FIG. 3C) and mSTING (FIG. 3D). Residues R238, Q266, and T267 are displayed for reference. FIG. 3E depicts a ribbon overlay comparing structures of mSTING (*) and hSTING (). FIG. 3F is a table of docking score comparisons with literature values for $hSTING^{WT}$ and $hSTING^{REF}$ isoforms. FIG. 3G is RMSF profiles between REF (*), WT (**), and AQ (*) isoforms of STING bound to 2,3-cGAMP. Residues for lid region shown as dashed lines.

Extensive MD simulations were performed to better understand how STING interacts with ligands and other potential binding partners. Some commonalities seem to arise from comparing trajectories between isoforms and control ligands leading to postulation on intracate binding mechanics. The main binding partners for STING in the IFN-β pathway are IRF3 and TBK1. A simple metric was devised to measure possible activation of STING by evaluating the distance between the alpha carbons of residue H185 at the end of the α2 helix. Crystal structures of known agonists present alpha carbon distances in the range of 34 to 38 Å. Apo crystal structures have alpha carbon distances in the range of 47 to 56 Å. Without limiting ourselves, the proposed binding mechanism is that initial binding is with the bottom of the CDN binding region near residues Q266 and T267. The initially disordered "lid" region comprising residues 154-244 (FIGS. 3A-3B, ribbon adjacent to *) interacts with the bound ligand and induces a β sheet formation, bringing the α2 helices closer together. The ligand then associates itself more with the ordered lid region, further stabilizing the conformation. It is because of this complicated binding mechanism that computational modeling proves difficult. Additional complexities arise when accounting for the different STING alleles. Profiles of RMSD per residue (FIG. 3G) from MD simulations show significant contrasts between the REF, WT, and AQ isoforms. The lid regions for REF and WT are substantially more disordered than AQ. This may be due to increased entropy from the glycine residue at the 230 position for REF and WT, opposed to alanine for AQ. This could account for some discrepancies between experimental binding energies and model calculations as current computational techniques cannot easily measure this.

Early studies on STING focused mainly on mSTING due to its high sequence homology (~89%). The present application describes a comparison of the crystal structures between mSTING and hSTING and found that, while the two forms have significant homology and structural similarities (FIG. 3E), the SiteMap analyses of the CDN binding site show that they have completely different binding site topologies (FIGS. 3C-3D).

To account for potential differences between STING isoforms, computational models were created using only those isoforms which had amino acid variations in the known STING binding site, residues 230 and 232. This lead to three main models, $hSTING^{WT}$ (G230, R232), $hSTING^{REF}$ (G230, R232H), and $hSTING^{AQ}$ (G230A, R232). No literature data was found for ITC $K_D$ values on control compounds (2,3-cGAMP, 2,2-cGAMP, and c-di-GMP) for the AQ variant. Since these values are imperative for proper model validation, $hSTING^{AQ}$ was not used for comparing model controls with literature values. Ligand binding analyses were performed using five different binding energy estimation algorithms (SP, XP, IFD, QPLD, and MM-GBSA) to evaluate theoretical binding energies of control conjoining compounds. RMSD profiles of MD trajectories fit well with crystallographic B-factors and MD models appear to better resolve binding energetics and comparisons to literature values (FIG. 3F). Statistical models were compiled based on deviation from known values and internal variance to adjust for docking and simulation error.

After comparing multiple docking algorithms between each model structure, SP docking was found to be the optimal coarse screen method using $hSTING^{REF}$ model due to a larger body of research material concerning the REF isoform needed for proper validation of computational modeling. The NCI diversity set V and ASINEX diversity sets were screened and a coarse-grained pharmocophore model was employed to rapidly scan the ZINC database using the ZINC Pharmer algorithm. Top hits were reviewed by team and best candidates were chosen for experimental testing to confirm hits. The compound NSC 335504 was among the initial hits and further assays were performed for verification.

Statistical models were compiled based on deviation from known values and internal variance to adjust for docking and simulation error. ITC, SPR, and virtual docking energetics for the native ligands 2'3'-cGAMP, 3.8 nM, 1.4 nM, 2.4 nM respectively, and c-di-GMP, 1.2 μM, 4.8 μM, and 4.6 μM respectively, agree with unequivocal precision lending substantial evidence to the validity of this binding model.

After comparing multiple docking algorithms between each model structure, SP docking was found to be the optimal coarse screen method using $hSTING^{REF}$ model due to a larger body of research material concerning the REF isoform needed for proper validation of computational modeling. The NCI diversity set V and ASINEX diversity sets were screened and a coarse-grained pharmacophore model was employed to rapidly scan the ZINC database using the ZINC Pharmer algorithm. Top hits were reviewed and best candidates were chosen for experimental testing to confirm hits. The compound NSC 335504 was among the initial hits and further assays were performed for verification.

Computational modeling predicted a binding affinity $k_D$ of 627 nM and an $EC_{50}$ of 9.1 μM from MD simulation H185 distance of 51.2 Å. Microscale Thermophoresis (MST) was performed as a rough initial estimate of binding affinity yielding a $K_D$ of 260±66 nM and SPR was then used to refine and confirm results with a $K_D$ of 430±140 nM (FIG. 3). The luciferase assay found an $EC_{50}$ of 29±1.6 μM for NSC 335504 (FIG. 3). Both direct binding assays and cell assays were well within agreement with computational models. Therefore, computational modeling can be heavily relied on for lead optimization for either agonists, partial agonists, or antagonists with the NSC 335504 scaffold.

In order to determine the activity of this compound, several biochemical assays were carried out. Assays showed binding of the compound to STING and cell-based assays exhibited down-regulation of IRF3 in comparison to 2,3-cGAMP.

Figure 4A:
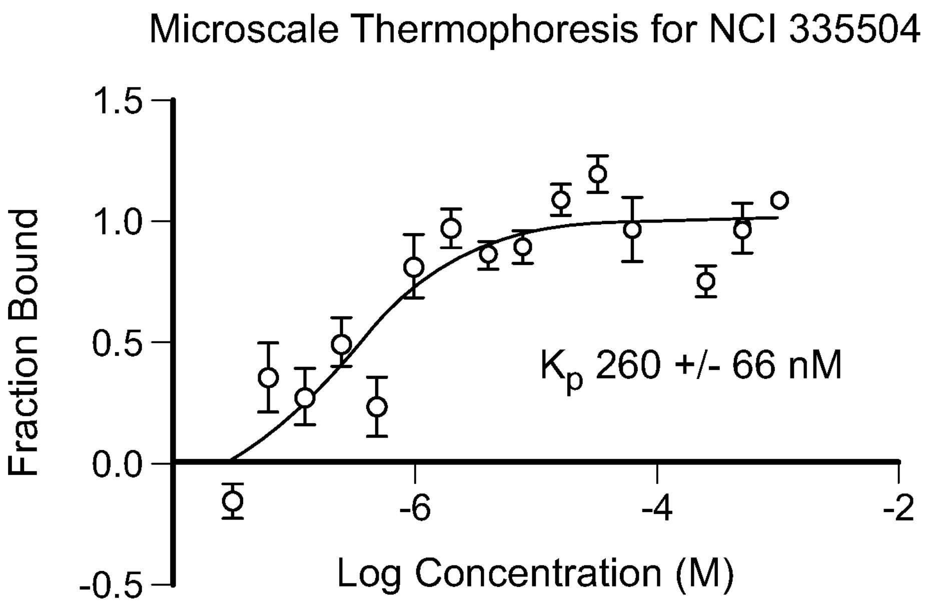
FIG. 4A depicts a plot showing the results of a microscale thermophoresis (MST) binding assay.
Figure 4B:
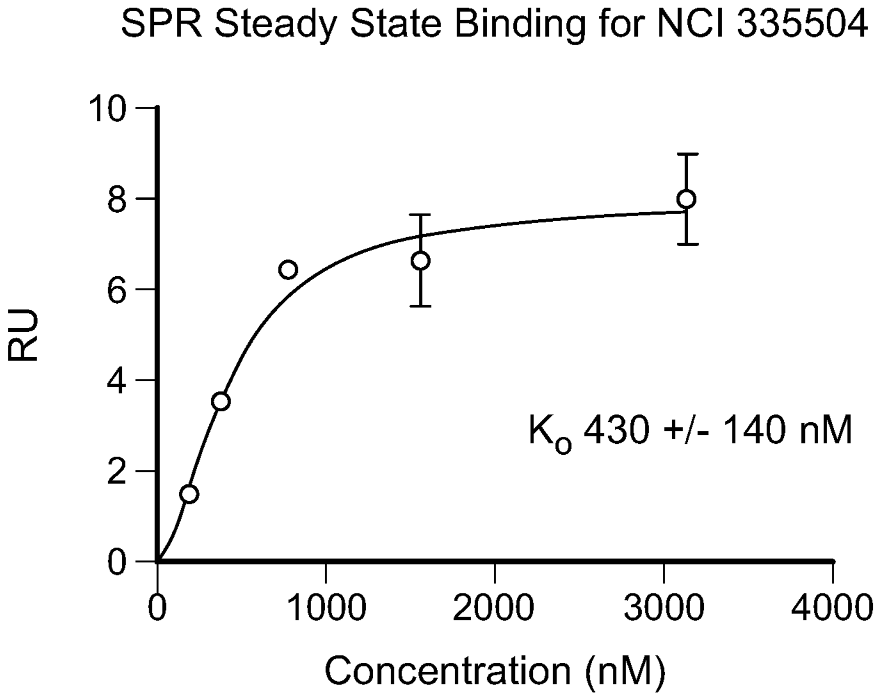
FIG. 4B depicts a plot of Surface Plasmon Resonance (SPR) steady state.
Figure 4C:
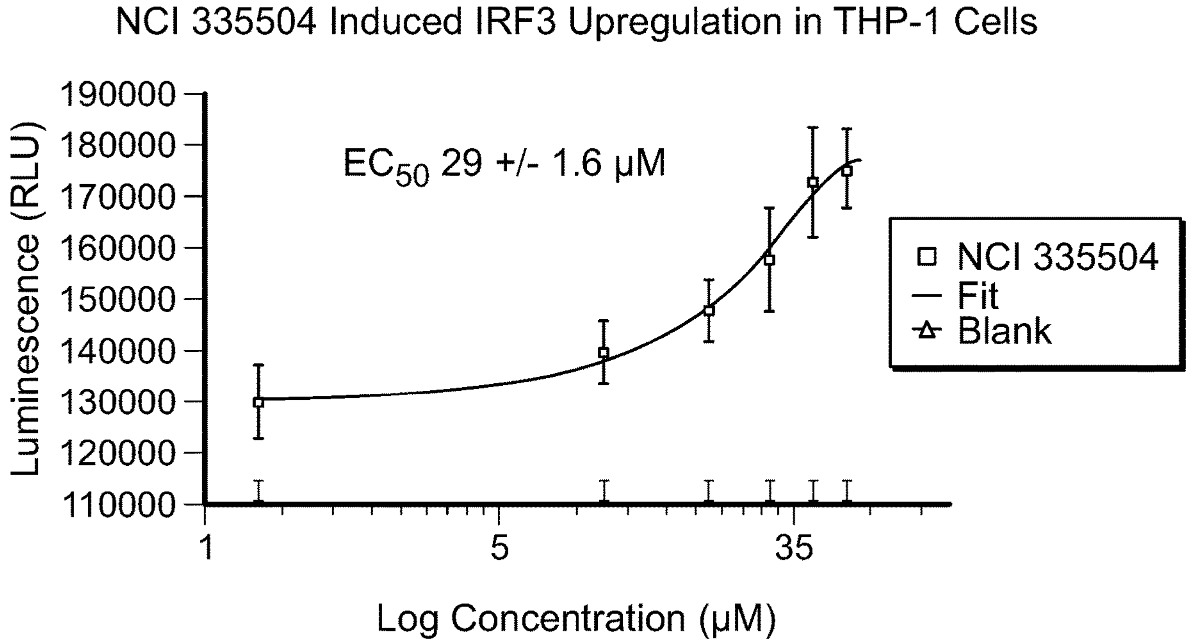
FIG. 4C depicts a plot of luminescence vs. log of concentration of a luciferase assay using monocytic leukemia THP-1 cells.
Figure 5A:
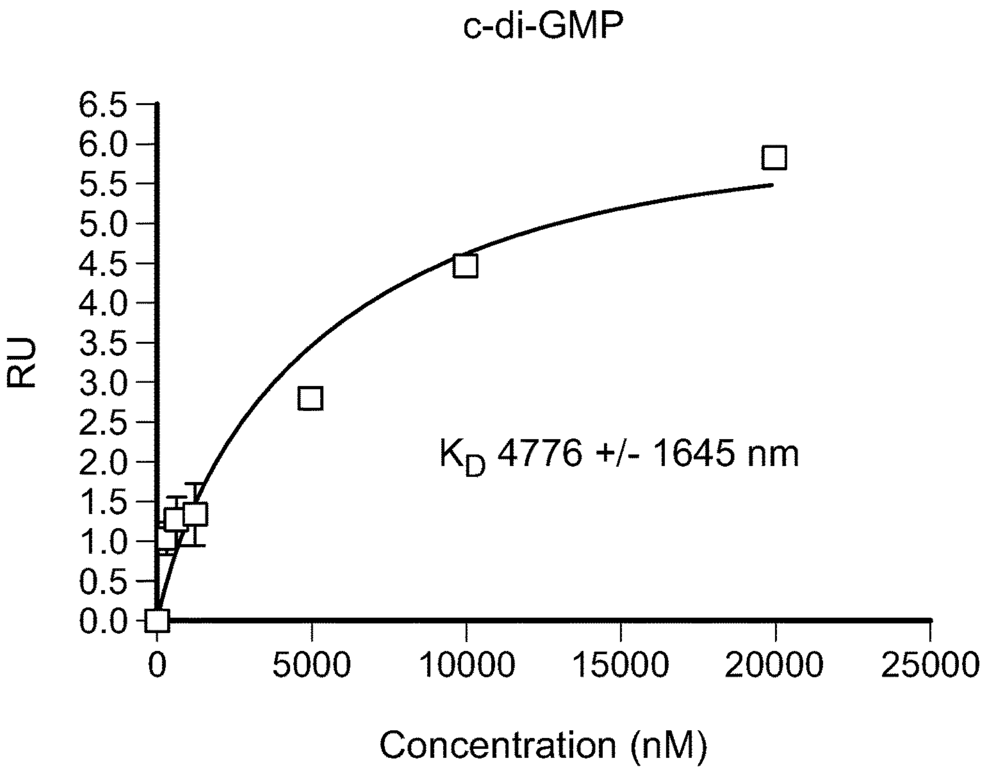
FIG. 5A depicts a binding affinity plot for c-di-GMP.
Figure 5B:
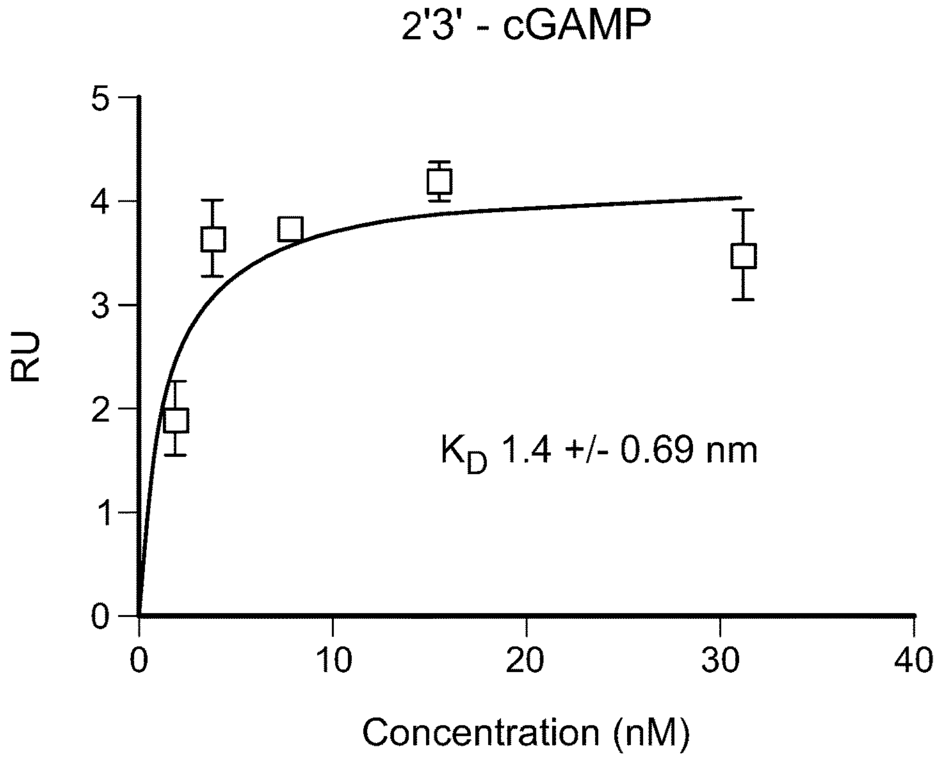
FIG. 5B depicts a binding affinity plot for c-di-GMP.

FIG. 4A depicts an MST binding assay. FIG. 4B depicts an SPR steady state using hill model. Hill coefficient determined as 1.738. FIG. 4C depicts a plot of luminescence vs. log of concentration of a luciferase assay utilizing monocytic leukemia THP-1 cells that was carried out to determine the regulation of interferon stimulated genes (ISG).

As shown in FIG. 4, a 50% increase in Luciferase activity was observed when compared to the blank. Because the luciferase assay is a direct measure if IRF-3 regulation, it can be assumed that IRF-3 is downregulated in proportion to the decrease in luminescence from the THP-1 cells. Once this is assumed, it can also be extrapolated that IFN-β will decrease as well, considering the downstream effects of IRF-3. An implication of these results is that, when compared to 2,3-cGAMP, the effect of 335504 is significantly lower. So while the compound upregulates the pathway slightly, it is actually an antagonist due to its ability to lower 2,3-cGAMP activity as shown in the competition assay (see discussion of FIG. 7 below).

To further cross-validate the direct binding of 335504 to hSTING, the binding affinity of 335504 with hSTING was measured by MST (FIG. 4), confirming that both the positive control, 2,3-cGAMP, and 335504 bind to hSTING while the competitive compound, c-di-GMP, binds but with lesser affinity. These results are also consistent with the SPR data (FIG. 5A-6B). FIGS. 5A-6B depict steady state SPR binding affinity plots for c-di-GMP and 2'3'-cGAMP, respectively.

Figure 6:
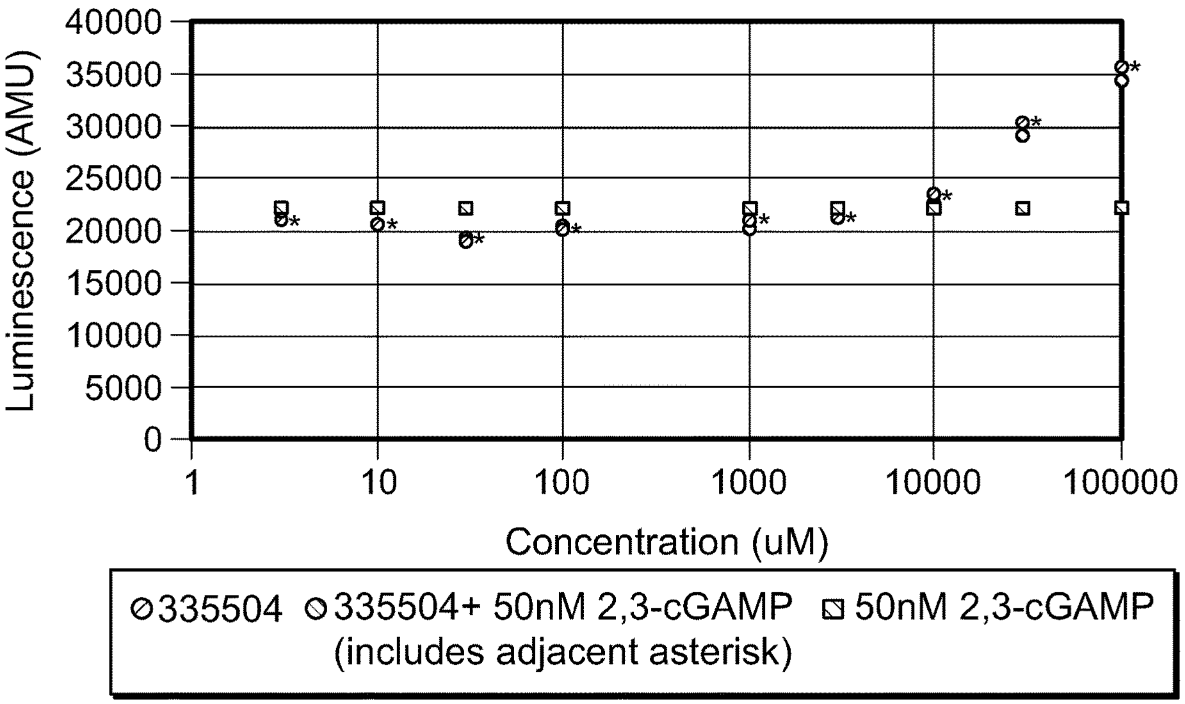
FIG. 6 depicts plots of luminescence vs. various concentrations of 335504 and known agonist 2,3-cGAMP from THP-1 monocytic leukemia cells.

FIG. 6 depicts the effect of various concentrations of 335504 and known agonist 2,3-cGAMP on luminescence measured from THP-1 monocytic leukemia cells. At single to double digit concentrations of 335504, competition of the compound with 2,3cGAMP can be observed. This effect, however, is not seen at higher concentrations due to the synergistic effect of the compounds on the IFN-β signaling pathway in these cells.

Figure 7:
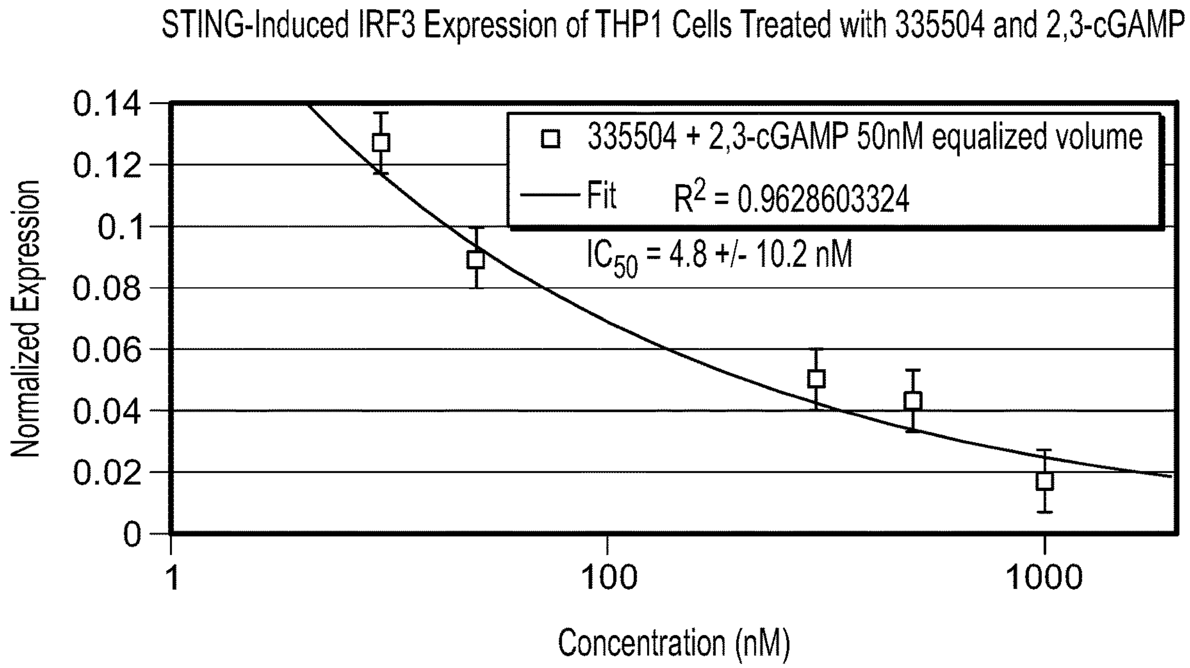
FIG. 7 depicts a plot of various concentrations of 335504 and known agonist 2,3-cGAMP on STING-induced IRF3 expression in THP-1 monocytic leukemia cells.

FIG. 7 shows the effect of various concentrations of 335504 and known agonist 2,3-cGAMP on STING-induced IRF3 expression in THP-1 monocytic leukemia cells, demonstrating an $IC_{50}$ of 335504 of about 4.8 nM±10.2 nM.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

REFERENCES

The following references are incorporated herein in their entirety:

Yi G. et al., 2013. PLoS One. 8:e77846.

Jin L. et al., 2011. Genes Immun. 12:263-9.

Zhang X. et al., 2013. Mol. Cell. 51:226-235.

Gao, Pu, et al. Cell 154.4 (2013): 748-762.

Chin, K-H., et al. Acta Crystallographica Section D: Biological Crystallography 69.3 (2013): 352-366.

Shu, Chang, et al. Nature structural and molecular biology 19.7 (2012): 722.

Shang, Guijun, et al. Nature structural and molecular biology 19.7 (2012): 725.

Sastry, G. M.; Adzhigirey, M.; Day, T.; Annabhimoju, R.; Sherman, W., *J. Comput. Aid. Mol. Des.,* 2013, 27(3), 221-234.

Li, Hui, Andrew D. Robertson, and Jan H. Jensen. *Proteins: Structure, Function, and Bioinformatics* 61.4 (2005): 704-721.

Shivakumar, D.; Williams, J.; Wu, Y.; Damm, W.; Shelley, J.; Sherman, W., *J. Chem. Theory Comput.,* 2010, 6, 1509-1519

Guo, Z.; Mohanty, U.; Noehre, J.; Sawyer, T. K.; Sherman, W.; Krilov, G., *Chem. Biol. Drug Des.,* 2010, 75, 348-359

Kevin J. Bowers, Edmond Chow, Huafeng Xu, Ron O. Dror, Michael P. Eastwood, Brent A. Gregersen, John L. Klepeis, Istvan Kolossvary, Mark A. Moraes, Federico D. Sacerdoti, John K. Salmon, Yibing Shan, and David E. Shaw, *Proceedings of the ACM/IEEE Conference on Supercomputing* (*SC*06), Tampa, Fla., 2006, November 11-17.

Price, Daniel J., and Charles L. Brooks III. *The Journal of chemical physics* 121.20 (2004): 10096-10103.

Harder, E.; Damm, W.; Maple, J.; Wu, C.; Reboul, M.; Xiang, J. Y.; Wang, L.; Lupyan, D.; Dahlgren, M. K.; Knight, J. L.; Kaus, J. W.; Cerutti, D. S.; Krilov, G.; Jorgensen, W. L.; Abel, R.; Friesner, R. A., *J. Chem. Theory Comput.,* 2015, DOI: 10.1021/acs.jctc.5b008641

Ryckaert, Jean-Paul, Giovanni Ciccotti, and Herman J C Berendsen. *Journal of Computational Physics* 23.3 (1977): 327-341.

Tuckerman, M. B. B. J. M., Bruce J. Berne, and Glenn J. Martyna. *The Journal of chemical physics* 97.3 (1992): 1990-2001.

Darden, T.; York, D.; Pedersen, L. Particle mesh ewald—an N. Log(N) method for Ewald sums in large systems. J. Chem. Phys. 1993, 98, 10089-10092

Essmann, U.; Perera, L.; Berkowitz, M. L.; Darden, T.; Lee, H.; Pedersen, L. G. A smooth particle mesh Ewald method. J. Chem. Phys. 1995, 103, 8577-8593

Nosé, Shuichi, and M. L. Klein. *Molecular Physics* 50.5 (1983): 1055-1076

Martyna, Glenn J., Douglas J. Tobias, and Michael L. Klein. *The Journal of Chemical Physics* 101.5 (1994): 4177-4189 && Martyna, Glenn J., et al. *Molecular Physics* 87.5 (1996): 1117-1157.

Ponder, Jay W., and Frederic M. Richards. *Journal of Computational Chemistry* 8.7 (1987): 1016-1024

Berendsen, H. J. C.; Postma, J. P. M.; van Gunsteren, W. F.; DiNola, A.; Haak, J. R. (1984). *Journal of Chemical Physics* 81 (8): 3684-3690.

Halgren, T., *J. Chem. Inf. Model.,* 2009, 49, 377-389

Halgren, T., *Chem. Biol. Drug Des.,* 2007, 69, 146-148.

Friesner, R. A.; Murphy, R. B.; Repasky, M. P.; Frye, L. L.; Greenwood, J. R.; Halgren, T. A.; Sanschagrin, P. C.; Mainz, D. T., *J. Med. Chem.,* 2006, 49, 6177-6196

Halgren, T. A.; Murphy, R. B.; Friesner, R. A.; Beard, H. S.; Frye, L. L.; Pollard, W. T.; Banks, J. L., *J. Med. Chem.,* 2004, 47, 1750-1759

Friesner, R. A.; Banks, J. L.; Murphy, R. B.; Halgren, T. A.; Klicic, J. J.; Mainz, D. T.; Repasky, M. P.; Knoll, E. H.; Shaw, D. E.; Shelley, M.; Perry, J. K.; Francis, P.; Shenkin, P. S., *J. Med. Chem.,* 2004, 47, 1739-1749.

Farid, R.; Day, T.; Friesner, R. A.; Pearlstein, R. A., *Bioorg. & Med. Chem.,* 2006, 14, 3160-3173

Sherman, W.; Day, T.; Jacobson, M. P.; Friesner, R. A.; Farid, R., *J. Med. Chem.,* 2006, 49, 534-553

Sherman, W.; Beard, H. S.; Farid, R., *Chemical Biology & Drug Design,* 2006, 67, 83-84.

Cho, A. E.; Guallar, V.; Berne, B.; Friesner, R. A., J. Comput. Chem., 2005, 26, 915-931.

Murphy, R. B.; Philipp, D. M.; Friesner, R. A., J. Comp. Chem., 2000, 21, 1442-1457

Philipp, D. M.; Friesner, R. A., J. Comp. Chem., 1999, 20, 1468-1494.

Qiu, Di, et al. The Journal of Physical Chemistry A 101.16 (1997): 3005-3014.

Conlon, Joseph, et al., The Journal of Immunology 190.10 (2013): 5216-5225.

Koes, David Ryan, and Carlos J. Camacho. Nucleic acids research 40.W1 (2012): W409-W414.

Tanaka, Yasuo, and Zhijian J. Chen. Science signaling 5.214 (2012): ra20-ra20.

Gao, D.; Li, T.; Li, X.-D.; Chen, X.; Li, Q.-Z.; Wight-Carter, M.; Chen, Z. *Proceedings of the National Academy of Sciences of the United States of America* 2015, E5699-E5705.

Zhou, R.; Xie, X.; Li, X.; Qin, Z.; Wei, C.; Liu, J.; Luo, Y *Infection, Genetics, and Evolution* 2020, 77, 104094.

Ahn, J.; Barber, G. *Current Opinion in Immunology* 2014, 31, 121-126.

Li, Q.-Z.; Zhou, J.; Lian, Y; Zhang, B.; Branch, V. K.; Can-Johnson, F.; Karp, D. R.; Mohan, C.; Wakeland, E. K.; Olsen, N. *J. Clin. Exp. Immunol.* 2010, 159(3), 281-291.

What is claimed is:

1. A compound of Formula (I), or a pharmaceutically acceptable salt thereof:

(I)

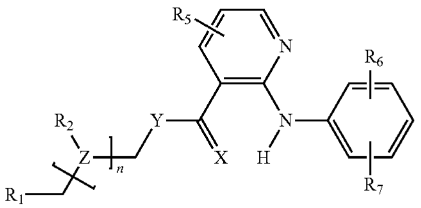

wherein:

X is O or $NR^{4A}$,

Y is O, $NR^{4A}$, $CH_2$, or absent;

Z is CH;

n is 0, 1, 2, or 3;

$R^1$ and $R^2$ are independently selected from OH, $OR^3$, and $OR^{3A}$, $R^3$ and each $R^{4A}$ are independently selected from hydrogen, C1-C10 alkyl optionally substituted with 1-6 halogens, C6-C10 aryl, and 5 to 10 membered heteroaryl;

$R^{3A}$ is

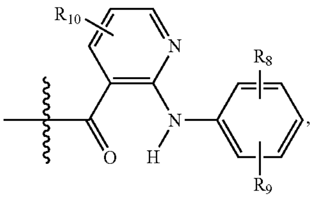

wherein ~ represents the point of connection of $R^{3A}$ to the remainder of the molecule;

$R^5$, $R^6$, $R^7$, $R^8$, $R^9$, and $R^{10}$ are independently selected from hydrogen, halogen, pseudohalogen, C1-C10 alkyl, and C6-C10 aryl;

wherein $R^1$ and $R^2$ are not both $OR^{3A}$; and wherein the compound of Formula (I), or a pharmaceutically acceptable salt thereof, is not NCS 335504,or a salt thereof:

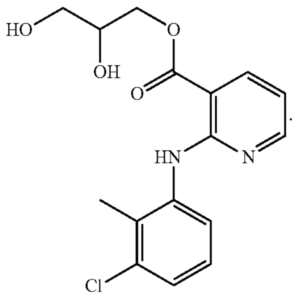 [SMILES: Cc1c(Cl)cccc1Nc1ncccc1C(=O)OCC(O)CO]

2. The compound of claim 1, wherein X is O.

3. The compound of claim 1, wherein Y is O.

4. The compound of claim 1, wherein Z is CH.

5. The compound of claim 1, wherein n is 2.

6. The compound of claim 1, wherein $R^1$ is $OR^{3A}$ and $R^2$ is selected from OH and $OR^3$.

7. The compound of claim 1, wherein $R^{3A}$ is

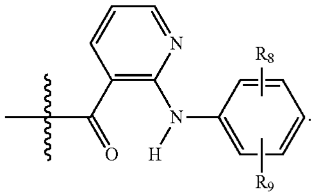

8. A compound of Formula (II), or a pharmaceutically acceptable salt thereof:

(II)

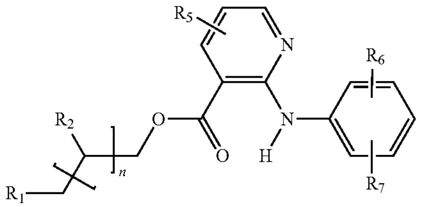

wherein:

$R^1$ is

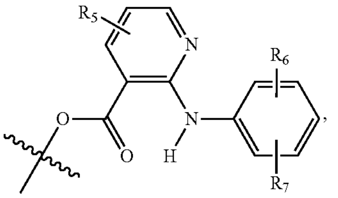

wherein ~ represents the point of connection of $R^1$ to the remainder of the molecule;

n is 0, 1, 2, or 3;

$R^2$ is hydrogen, OH, $OR^3$, $SR^3$, or $NR^3R^4$;

$R^3$ and $R^4$ are independently selected from hydrogen, C1-C10 alkyl optionally substituted with 1-6 halogens, C6-C10 aryl, and 5 to 10 membered heteroaryl; or $R^3$ and $R^4$, together with the nitrogen atom to which they are attached, can come together to form a 3 to 7 membered heterocyclyl or 5 to 10 membered heteroaryl; and $R^5$, $R^6$, $R^7$, $R^8$, $R^9$, and $R^{10}$ are independently selected from hydrogen, halogen, pseudohalogen, C1-C10 alkyl optionally substituted with 1-6 halogens, C6-C10 aryl, and 5 to 10 membered heteroaryl.

9. The compound of claim 1, wherein $R^5$ is halogen.

10. The compound of claim 1, wherein $R^5$ is C1-C10 alkyl.

11. The compound of claim 1, wherein $R^6$ is halogen.

12. The compound of claim 1, wherein $R^7$ is halogen.

13. The compound of claim 1, wherein $R^8$ is halogen.

14. The compound of claim 1, wherein $R^9$ is C1-C10 alkyl.

15. The compound of claim 1, wherein $R^{10}$ is halogen.

16. The compound of claim 1, wherein $R^{10}$ is C1-C10 alkyl.

17. A pharmaceutical composition comprising a compound of claim 1, or a pharmaceutically acceptable salt thereof, and at least one excipient.

18. A method of treating cancer in a subject in need thereof, comprising administering a therapeutically effective amount of a compound of claim 1, or a pharmaceutically acceptable salt thereof, to the subject.

19. A method of treating an autoimmune disorder in a subject in need thereof, comprising administering a therapeutically effective amount of a compound of claim 1, or a pharmaceutically acceptable salt thereof, to the subject.

20. The compound of claim 8, wherein the compound is

1

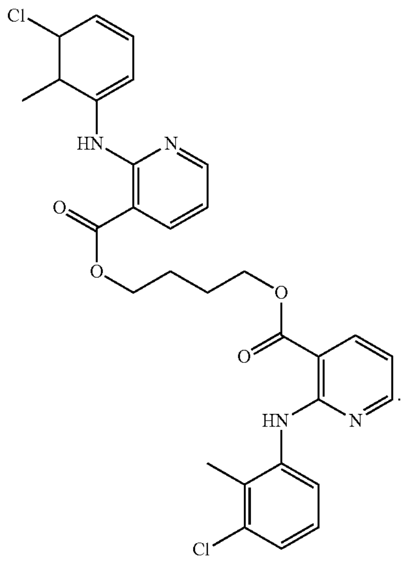

21. The compound of claim 8, wherein the compound is

2

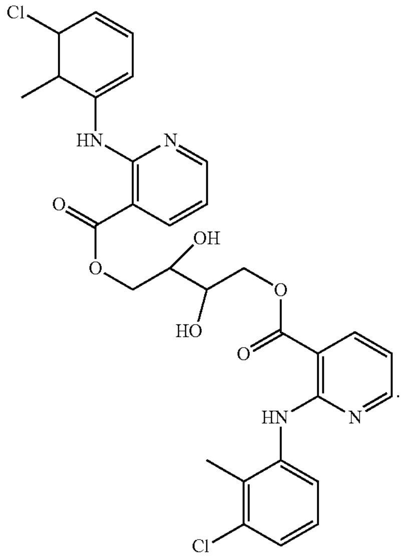

* * * * *